United States Patent
Rajani

(10) Patent No.: US 11,268,104 B2
(45) Date of Patent: Mar. 8, 2022

(54) TRANSGENIC PLANTS WITH ENHANCED TRAITS

(71) Applicant: Monsanto Technology LLC, St. Louis, MO (US)

(72) Inventor: Monnanda Somaiah Rajani, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 131 days.

(21) Appl. No.: 16/555,255

(22) Filed: Aug. 29, 2019

(65) Prior Publication Data

US 2019/0382783 A1    Dec. 19, 2019

Related U.S. Application Data

(63) Continuation of application No. 15/027,821, filed as application No. PCT/US2014/059261 on Oct. 6, 2014, now abandoned.

(60) Provisional application No. 61/932,941, filed on Jan. 29, 2014, provisional application No. 61/887,552, filed on Oct. 7, 2013.

(51) Int. Cl.
*C12N 15/82*    (2006.01)
*C07K 14/415*    (2006.01)

(52) U.S. Cl.
CPC ........ *C12N 15/8261* (2013.01); *C07K 14/415* (2013.01); *C12N 15/8241* (2013.01); *C12N 15/8273* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 7,825,296 B2 | 11/2010 | Jiang et al. | |
| 8,030,546 B2 | 10/2011 | Reuber et al. | |
| 2006/0272060 A1 | 11/2006 | Heard et al. | |
| 2007/0006337 A1 | 1/2007 | Cook et al. | |
| 2009/0138981 A1* | 5/2009 | Repetti ................ | C07K 14/415 800/263 |
| 2010/0186106 A1 | 7/2010 | Creelman et al. | |
| 2012/0137382 A1 | 5/2012 | Repetti et al. | |

FOREIGN PATENT DOCUMENTS

EP    1887081    2/2008
WO    WO 2009/073069 A2    6/2009

OTHER PUBLICATIONS

Angenon et al. (FEBS letters 271.1-2(1990): 144-146). (Year: 1990).*
Moose, et al. "Biotechnology approaches to improving maize nitrogen use efficiency." Molecular genetic approaches to maize improvement. Springer, Berlin, Heidelberg, 2009. 65-77. (Year: 2009).*
Angenon et al., "Analysis of the stop codon context in plant nuclear genes." *FEBS letters* 271.1-2 (1990): 144-146.
Al-Naggar et al., "Recurrent selection for drought tolerance improves maize productivity under low-N conditions." *Egypt. J. Plant Breed* 13 (2009): 53-70.
GenBank Accession NP_173506, submitted Feb. 18, 2011.
GenBank Accession XM_003543323, submitted Nov. 8, 2011.
Lindemose et al., "Structure, function and networks of transcription factors involved in abiotic stress responses." *International journal of molecular sciences* 14.3 (2013): 5842-5878.
Moose et al., "Biotechnology approaches to improving maize nitrogen use efficiency." *Molecular genetic approaches to maize improvement*. Springer, Berlin, Heidelberg, 2009. 65-77.
Ogata et al., The cavity in the hydrophobic core of Myb DNA-binding domain is reserved for DNA recognition and trans-activation, *Nature Structural biology*, 3:2, p. 178 to 187, 1996.
Sakura et al., Delineation of three functional domains of the transcriptional activator encoded by the c-myb protooncogene, *PNAS*, 86, p. 5758 to 5762, 1989.
Zimmerman et al., Comprehensive identification of *Arabidopsis thaliana* MYB transcription factors interacting with R/B-like BHLH proteins, *The Plant Journal*, 40, p. 22 to 34, 2004.

* cited by examiner

*Primary Examiner* — Charles Logsdon
(74) *Attorney, Agent, or Firm* — Morrison & Foerster LLP

(57)    ABSTRACT

This disclosure provides transgenic plants having enhanced traits such as increased yield, increased nitrogen use efficiency and enhanced drought tolerance; propagules, progeny and field crops of such transgenic plants; and methods of making and using such transgenic plants. This disclosure also provides methods of producing seed from such transgenic plants, growing such seed and selecting progeny plants with enhanced traits. Also disclosed are transgenic plants with altered phenotypes which are useful for screening and selecting transgenic events for the desired enhanced trait.

21 Claims, No Drawings
Specification includes a Sequence Listing.

SEQUENCE LISTING

<160> NUMBER OF SEQ ID NOS: 20

<210> SEQ ID NO 1
<211> LENGTH: 594
<212> TYPE: DNA
<213> ORGANISM: Arabidopsis thaliana

<400> SEQUENCE: 1

```
atggctcgcc ttctctttcg tcttctcgta gaatccaaca ctccgtctcc ggcgattgat    60
aactccaccg ccgcgttgaa ttctgatctc gtcgtcatcc tcgctgctct cctctgcgcc   120
ttgatttgcg ttctcggctt aatcgccgtt tctcgatgtg tctggctccg tcgtctcgca   180
gccggaaaca gaacagtctc cggatctcaa actcaatctc ctcaacctcc ggtggcagcg   240
gcgaacaaag gcctgaagaa gaaagtcctt caatctctcc cgaagcttac gttctcgcca   300
gagtcacctg agtcggagaa attcgcagag tgcgcgatct gtctagctga attctctgcc   360
ggcgacgagc tccgagtttt accgcagtgt ggtcacgggg tccacgtggc ttgcattgac   420
acgtggctag atctcactc gtcttgccct tcttgccgtc agatcttggt tgttgccagg   480
tgtcacaagt gtggagggtt t acccggtagc tctagctccg gacttgaatc cgaacccgaa   540
atcgagatcc gaatcaagca aggcgaagat gaccccaact ccttcttgcc atag         594
```

<210> SEQ ID NO 2
<211> LENGTH: 197
<212> TYPE: PRT
<213> ORGANISM: Arabidopsis thaliana

<400> SEQUENCE: 2

```
Met Ala Arg Leu Leu Phe Arg Leu Leu Val Glu Ser Asn Thr Pro Ser
1               5                  10                  15

Pro Ala Ile Asp Asn Ser Thr Ala Ala Leu Asn Ser Asp Leu Val Val
            20                  25                  30

Ile Leu Ala Ala Leu Leu Cys Ala Leu Ile Cys Val Leu Gly Leu Ile
        35                  40                  45

Ala Val Ser Arg Cys Val Trp Leu Arg Arg Leu Ala Ala Gly Asn Arg
    50                  55                  60

Thr Val Ser Gly Ser Gln Thr Gln Ser Pro Gln Pro Val Ala Ala
65                  70                  75                  80

Ala Asn Lys Gly Leu Lys Lys Val Leu Gln Ser Leu Pro Lys Leu
                85                  90                  95

Thr Phe Ser Pro Glu Ser Pro Glu Ser Glu Lys Phe Ala Glu Cys Ala
                100                 105                 110

Ile Cys Leu Ala Glu Phe Ser Ala Gly Asp Glu Leu Arg Val Leu Pro
            115                 120                 125

Gln Cys Gly His Gly Phe His Val Ala Cys Ile Asp Thr Trp Leu Gly
        130                 135                 140

Ser His Ser Ser Cys Pro Ser Cys Arg Gln Ile Leu Val Val Ala Arg
145                 150                 155                 160

Cys His Lys Cys Gly Gly Leu Pro Gly Ser Ser Ser Gly Leu Glu
                165                 170                 175
```

Ser Glu Pro Glu Ile Glu Ile Arg Ile Lys Gln Gly Glu Asp Pro
            180                 185                 190

Asn Ser Phe Leu Pro
        195

<210> SEQ ID NO 3
<211> LENGTH: 711
<212> TYPE: DNA
<213> ORGANISM: Arabidopsis thaliana

<400> SEQUENCE: 3

```
atgtcttaca gtgacccaaa ccaaaacccg attccagaaa cttacgctcc atcaaactca      60
actgaatcag agaaactgaa actttaccaa gcttttatct tctctgttcc aatctgtttc     120
acattcatcg ttctcttcgt tctttacgtc atttaccttc gtcgaaacag caccaccaat     180
gttgattggt cttctcttgg catgcgtggt ggtacctttg tccccaccaa caacaatctc     240
tcaacggctg aattaggact gagcaaagat attagagaga tgcttcctgt tgtcatctac     300
aaggagagtt tcatagtcaa agattcacaa tgttcagtgt gtcttgggga ctaccaagca     360
gaagagaaac tccaacaaat gccatcatgt gggcacactt ttcacatgga atgtattgat     420
ctatggctca catcacacac aacatgccct ctttgtcgtc tctctcttat ccccaaaccg     480
tccctagacc tgtcccatca agcacagag attgtctctt ccatagaaaa ctctaatgga     540
ggagaagctt caactcaacc agattcccag tcagcaaccg aagcaataag tcacaccgat     600
gatgtcgaag aaggtaaccg atagtcaa gaggtctcta aggagacgga agagaatgac      660
cgaaacagcg tagggacatc tgatggttgt tgtacttgta gacttggtta g            711
```

<210> SEQ ID NO 4
<211> LENGTH: 236
<212> TYPE: PRT
<213> ORGANISM: Arabidopsis thaliana

<400> SEQUENCE: 4

Met Ser Tyr Ser Asp Pro Asn Gln Asn Pro Ile Pro Glu Thr Tyr Ala
1               5                   10                  15

Pro Ser Asn Ser Thr Glu Ser Glu Lys Leu Lys Leu Tyr Gln Ala Phe
            20                  25                  30

Ile Phe Ser Val Pro Ile Cys Phe Thr Phe Ile Val Leu Phe Val Leu
        35                  40                  45

Tyr Val Ile Tyr Leu Arg Arg Asn Ser Thr Thr Asn Val Asp Trp Ser
    50                  55                  60

Ser Leu Gly Met Arg Gly Gly Thr Phe Val Pro Thr Asn Asn Asn Leu
65                  70                  75                  80

Ser Thr Ala Glu Leu Gly Leu Ser Lys Asp Ile Arg Glu Met Leu Pro
                85                  90                  95

Val Val Ile Tyr Lys Glu Ser Phe Ile Val Lys Asp Ser Gln Cys Ser
            100                 105                 110

Val Cys Leu Gly Asp Tyr Gln Ala Glu Glu Lys Leu Gln Gln Met Pro
        115                 120                 125

Ser Cys Gly His Thr Phe His Met Glu Cys Ile Asp Leu Trp Leu Thr
    130                 135                 140

Ser His Thr Thr Cys Pro Leu Cys Arg Leu Ser Leu Ile Pro Lys Pro
145                 150                 155                 160

Ser Leu Asp Leu Ser His Gln Ser Thr Glu Ile Val Ser Ser Ile Glu
                165                 170                 175

Asn Ser Asn Gly Gly Glu Ala Ser Thr Gln Pro Asp Ser Gln Ser Ala
            180                 185                 190

Thr Glu Ala Ile Ser His Thr Asp Asp Val Glu Glu Gly Asn Arg Asp
        195                 200                 205

Ser Gln Glu Val Ser Lys Glu Thr Glu Glu Asn Asp Arg Asn Ser Val
        210                 215                 220

Gly Thr Ser Asp Gly Cys Cys Thr Cys Arg Leu Gly
225                 230                 235

<210> SEQ ID NO 5
<211> LENGTH: 885
<212> TYPE: DNA
<213> ORGANISM: Arabidopsis thaliana

<400> SEQUENCE: 5

```
atggaggaag gaacttcagg ttcacggaga acacggtctc aagttgctcc agaatgggca      60
gtcaaagatt gtctagtcct cgtgaatgag atcgctgcgg ttgaagccga ttgttcgaat     120
gctttatcta gcttccagaa atggacaatg atcacagaga actgcaacgc tttggatgtt     180
agcagaaatc taaaccaatg caggaggaaa tgggattctt tgatgtctga ttacaatcag     240
atcaagaagt gggaatctca gtaccgaggc actggtcgtt cctattggtc cctgagtagt     300
gacaagagga agttacttaa tctcccgggg gatatcgata tcgagctttt tgaagccatc     360
aatgcggttg tgatgatcca agatgaaaaa gctgggactg aatctgatag tgaccctgaa     420
gcgcaagacg ttgttgatct ctctgctgaa ttagcttttg taggatcaaa aagatcaaga     480
cagcgaacaa tggtcatgaa ggagacaaag aagaagagc cacggactag ccgagttcaa     540
gtaaacactc gagagaaacc tataactaca aaagcaaccc atcagaacaa accatggga     600
gagaagaagc cggtggaaga tatgtccaca gatgaagaag aagatgaaac aatgaacata     660
gaagaggatg tagaagtgat ggaagcgaag ctaagttata aaattgactt gatacatgcg     720
atagtcggga gaaatctagc aaaggataat gaaacaaagg atggtgttag tatggacgac     780
aagttgaagt ctgtgagaca gcaaggagac gagctcatcg gttgtctgag tgaaattgtt     840
agtacccta taggcttca tgaagttcca caagaaatcg agtag                      885
```

<210> SEQ ID NO 6
<211> LENGTH: 294
<212> TYPE: PRT
<213> ORGANISM: Arabidopsis thaliana

<400> SEQUENCE: 6

Met Glu Glu Gly Thr Ser Gly Ser Arg Arg Thr Arg Ser Gln Val Ala
1               5                   10                  15

Pro Glu Trp Ala Val Lys Asp Cys Leu Val Leu Val Asn Glu Ile Ala
            20                  25                  30

Ala Val Glu Ala Asp Cys Ser Asn Ala Leu Ser Ser Phe Gln Lys Trp
        35                  40                  45

Thr Met Ile Thr Glu Asn Cys Asn Ala Leu Asp Val Ser Arg Asn Leu
    50                  55                  60

Asn Gln Cys Arg Arg Lys Trp Asp Ser Leu Met Ser Asp Tyr Asn Gln
65                  70                  75                  80

Ile Lys Lys Trp Glu Ser Gln Tyr Arg Gly Thr Gly Arg Ser Tyr Trp
                85                  90                  95

Ser Leu Ser Ser Asp Lys Arg Lys Leu Leu Asn Leu Pro Gly Asp Ile
            100                 105                 110

```
Asp Ile Glu Leu Phe Glu Ala Ile Asn Ala Val Val Met Ile Gln Asp
        115                 120                 125

Glu Lys Ala Gly Thr Glu Ser Asp Ser Asp Pro Glu Ala Gln Asp Val
130                 135                 140

Val Asp Leu Ser Ala Glu Leu Ala Phe Val Gly Ser Lys Arg Ser Arg
145                 150                 155                 160

Gln Arg Thr Met Val Met Lys Glu Thr Lys Glu Glu Pro Arg Thr
                165                 170                 175

Ser Arg Val Gln Val Asn Thr Arg Glu Lys Pro Ile Thr Thr Lys Ala
                180                 185                 190

Thr His Gln Asn Lys Thr Met Gly Glu Lys Lys Pro Val Glu Asp Met
        195                 200                 205

Ser Thr Asp Glu Glu Glu Asp Glu Thr Met Asn Ile Glu Glu Asp Val
    210                 215                 220

Glu Val Met Glu Ala Lys Leu Ser Tyr Lys Ile Asp Leu Ile His Ala
225                 230                 235                 240

Ile Val Gly Arg Asn Leu Ala Lys Asp Asn Glu Thr Lys Asp Gly Val
                245                 250                 255

Ser Met Asp Asp Lys Leu Lys Ser Val Arg Gln Gln Gly Asp Glu Leu
                260                 265                 270

Ile Gly Cys Leu Ser Glu Ile Val Ser Thr Leu Asn Arg Leu His Glu
            275                 280                 285

Val Pro Gln Glu Ile Glu
    290

<210> SEQ ID NO 7
<211> LENGTH: 942
<212> TYPE: DNA
<213> ORGANISM: Arabidopsis thaliana

<400> SEQUENCE: 7
atggcaaaag tctctgggag gagcaagaaa acaatcgttg acgatgaaat cagcgataaa      60
acagcgtctg cgtctgagtc tgcgtccatt gccttaacat ccaaacgcaa acgtaagtcg     120
ccgcctcgaa cgctcctctc tcaacgcagc tccccttaca gaggcgtcac aaggcataga     180
tggactggga gatacgaagc gcatttgtgg gataagaaca gctggaacga tacacagacc     240
aagaaaggac gtcaagttta tctagggcct tacgacgaag aagaagcagc agcacgtgcc     300
tacgacttag cagcattgaa gtactgggga cgagacacac tcttgaactt cccttttgccg    360 agttatgacg aagacgtcaa agaaatggaa ggccaatcca aggaagagta tattggatca     420
ttgagaagaa aaagtagtgg attttctcgc ggtgtatcaa atacagagg cgttgcaagg      480 catcaccata tgggagatg ggaagctaga attggaaggg tgtttggtaa taaatatcta      540
tatcttggaa catacgccac gcaagaagaa gcagcaatcg cctacgacat cgcggcaata     600
gagtaccgtg gacttaacgc cgttaccaat ttcgacgtca gccgttatct aaaccctaac     660
gccgccgcgg ataaagccga ttccgattct aagcccattc gaagccctag tcgcgagccc     720
gaatcgtcgg atgataacaa atctccgaaa tcagaggaag taatcgaacc atctacatcg     780
ccggaagtga ttccaactcg ccggagcttc cccgacgata tccagacgta ttttgggtgt     840
caagattccg gcaagttagc gactgaggaa gacgtaatat cgattgtttt caattcttat     900
ataaatcctg gcttctataa cgagtttgat tatggaccct ag                        942
```

<210> SEQ ID NO 8
<211> LENGTH: 313
<212> TYPE: PRT
<213> ORGANISM: Arabidopsis thaliana

<400> SEQUENCE: 8

```
Met Ala Lys Val Ser Gly Arg Ser Lys Lys Thr Ile Val Asp Asp Glu
1               5                   10                  15

Ile Ser Asp Lys Thr Ala Ser Ala Ser Glu Ser Ala Ser Ile Ala Leu
            20                  25                  30

Thr Ser Lys Arg Lys Arg Lys Ser Pro Pro Arg Asn Ala Pro Leu Gln
        35                  40                  45

Arg Ser Ser Pro Tyr Arg Gly Val Thr Arg His Arg Trp Thr Gly Arg
    50                  55                  60

Tyr Glu Ala His Leu Trp Asp Lys Asn Ser Trp Asn Asp Thr Gln Thr
65                  70                  75                  80

Lys Lys Gly Arg Gln Val Tyr Leu Gly Ala Tyr Asp Glu Glu Glu Ala
                85                  90                  95

Ala Ala Arg Ala Tyr Asp Leu Ala Ala Leu Lys Tyr Trp Gly Arg Asp
            100                 105                 110

Thr Leu Leu Asn Phe Pro Leu Pro Ser Tyr Asp Glu Asp Val Lys Glu
        115                 120                 125

Met Glu Gly Gln Ser Lys Glu Glu Tyr Ile Gly Ser Leu Arg Arg Lys
    130                 135                 140

Ser Ser Gly Phe Ser Arg Gly Val Ser Lys Tyr Arg Gly Val Ala Arg
145                 150                 155                 160

His His His Asn Gly Arg Trp Glu Ala Arg Ile Gly Arg Val Phe Gly
                165                 170                 175

Asn Lys Tyr Leu Tyr Leu Gly Thr Tyr Ala Thr Gln Glu Glu Ala Ala
            180                 185                 190

Ile Ala Tyr Asp Ile Ala Ala Ile Glu Tyr Arg Gly Leu Asn Ala Val
        195                 200                 205

Thr Asn Phe Asp Val Ser Arg Tyr Leu Asn Pro Asn Ala Ala Ala Asp
    210                 215                 220

Lys Ala Asp Ser Asp Ser Lys Pro Ile Arg Ser Pro Ser Arg Glu Pro
225                 230                 235                 240

Glu Ser Ser Asp Asp Asn Lys Ser Pro Lys Ser Glu Val Ile Glu
                245                 250                 255

Pro Ser Thr Ser Pro Glu Val Ile Pro Thr Arg Arg Ser Phe Pro Asp
            260                 265                 270

Asp Ile Gln Thr Tyr Phe Gly Cys Gln Asp Ser Gly Lys Leu Ala Thr
        275                 280                 285

Glu Glu Asp Val Ile Phe Asp Cys Phe Asn Ser Tyr Ile Asn Pro Gly
    290                 295                 300

Phe Tyr Asn Glu Phe Asp Tyr Gly Pro
305                 310
```

<210> SEQ ID NO 9
<211> LENGTH: 903
<212> TYPE: DNA
<213> ORGANISM: Arabidopsis thaliana

<400> SEQUENCE: 9

```
atgtcttcca tcccaaatag gttcaatatt tatggtggtg ataccacaaa ccatcgtgaa    60
tcgcttccca tcgaaatgaa tcacaactct cgaatggttc gatccatgtt cattacatct   120
```

```
gatcgcatga atcatagaga tttgttttct tctcctcctt ctttctcttc ttatcaaaat    180
tcacatatct cttcatcttc tgttgggttt aataattcac atatgactta tcatatgctg    240
aaaagaaatt atgattctgt ttcccgtgct gattatttct ctactaaaga tcattctcat    300
tttactcaag tatctttcac tcaaaccatc acaaataagt atactactat tgttccttcc    360
aatatatttg acactgttca ctatgatatt ggtcgtgtca aacgtgccat agattttaga    420
aatatttgga atcctaaatc tcatcttcca aaaaaattta ataggcaatg cgagattttg    480
aatcctaccc ctcttaatat cgtctttccg caccaggatt cagctgatcg tcaacattta    540
gacattattt tctcgtcatc aaagcacaac catgttttcc aagatggtcg atccttgaag    600
aaaatttccg aaccaaccaa tctgtttgaa aaatctaatt cttatgattc tcaagaagat    660
gagaaaatcg atgcttatca aatgatggt cgtacacata gtctaccgta tacgaaatac    720
ggtccatata catgtcccag gtgtaacggt gtgtttgata cttctcaaaa atttgctgca    780
catatgttat ctcactacaa taatgagacg gacaaagaaa gagaccaaag atttcgtgca    840
agaaataaaa aacgatatcg taagtttatg gacagtctta aatatcaaa acagaagata    900 tag    903
```

<210> SEQ ID NO 10
<211> LENGTH: 300
<212> TYPE: PRT
<213> ORGANISM: Arabidopsis thaliana

<400> SEQUENCE: 10

```
Met Ser Ser Ile Pro Asn Arg Phe Asn Ile Tyr Gly Gly Asp Thr Thr
 1               5                  10                  15

Asn His Arg Glu Ser Leu Pro Ile Glu Met Asn His Asn Ser Arg Met
            20                  25                  30

Val Arg Ser Met Phe Ile Thr Ser Asp Arg Met Asn His Arg Asp Leu
        35                  40                  45

Phe Ser Ser Pro Pro Ser Phe Ser Ser Tyr Gln Asn Ser His Ile Ser
    50                  55                  60

Ser Ser Ser Val Gly Phe Asn Asn Ser His Met Thr Tyr His Met Leu
65                  70                  75                  80

Lys Arg Asn Tyr Asp Ser Val Ser Arg Ala Asp Tyr Phe Ser Thr Lys
                85                  90                  95

Asp His Ser His Phe Thr Gln Val Ser Phe Thr Gln Thr Ile Thr Asn
            100                 105                 110

Lys Tyr Thr Thr Ile Val Pro Ser Asn Ile Phe Asp Thr Val His Tyr
        115                 120                 125

Asp Ile Gly Arg Val Lys Arg Ala Ile Asp Phe Arg Asn Ile Trp Asn
    130                 135                 140

Pro Lys Ser His Leu Pro Lys Lys Phe Asn Arg Gln Cys Glu Ile Leu
145                 150                 155                 160

Asn Pro Thr Pro Leu Asn Ile Val Phe Pro His Gln Asp Ser Ala Asp
                165                 170                 175

Arg Gln His Leu Asp Ile Ile Phe Ser Ser Ser Lys His Asn His Val
            180                 185                 190

Phe Gln Asp Gly Arg Ser Leu Lys Lys Ile Ser Glu Pro Thr Asn Leu
        195                 200                 205

Phe Glu Lys Ser Asn Ser Tyr Asp Ser Gln Glu Asp Glu Lys Ile Asp
    210                 215                 220
```

```
Ala Tyr Gln Tyr Asp Gly Arg Thr His Ser Leu Pro Tyr Thr Lys Tyr
225                 230                 235                 240

Gly Pro Tyr Thr Cys Pro Arg Cys Asn Gly Val Phe Asp Thr Ser Gln
            245                 250                 255

Lys Phe Ala Ala His Met Leu Ser His Tyr Asn Asn Glu Thr Asp Lys
        260                 265                 270

Glu Arg Asp Gln Arg Phe Arg Ala Arg Asn Lys Lys Arg Tyr Arg Lys
    275                 280                 285

Phe Met Asp Ser Leu Lys Ile Ser Lys Gln Lys Ile
    290                 295                 300

<210> SEQ ID NO 11
<211> LENGTH: 291
<212> TYPE: PRT
<213> ORGANISM: Arabidopsis thaliana

<400> SEQUENCE: 11

Met Glu Glu Gly Thr Ser Gly Ser Arg Arg Thr Arg Ser Gln Val Ala
1               5                   10                  15

Pro Glu Trp Ala Val Lys Asp Cys Leu Val Leu Asn Glu Ile Ala
            20                  25                  30

Ala Val Glu Ala Asp Cys Ser Asn Ala Leu Ser Ser Phe Gln Lys Trp
        35                  40                  45

Thr Met Ile Thr Glu Asn Cys Asn Ala Leu Asp Val Ser Arg Asn Leu
    50                  55                  60

Asn Gln Cys Arg Arg Lys Trp Asp Ser Leu Met Ser Asp Tyr Asn Gln
65                  70                  75                  80

Ile Lys Lys Trp Glu Ser Gln Tyr Arg Gly Thr Gly Arg Ser Tyr Trp
                85                  90                  95

Ser Leu Ser Ser Asp Lys Arg Lys Leu Leu Asn Leu Pro Gly Asp Ile
            100                 105                 110

Asp Ile Glu Leu Phe Glu Ala Ile Asn Ala Val Val Met Ile Gln Asp
        115                 120                 125

Glu Lys Ala Gly Thr Glu Ser Asp Ser Asp Pro Glu Ala Gln Asp Val
    130                 135                 140

Val Asp Leu Ser Ala Glu Leu Gly Ser Lys Arg Ser Arg Gln Arg Thr
145                 150                 155                 160

Met Val Met Lys Glu Thr Lys Lys Glu Glu Pro Arg Thr Ser Arg Val
                165                 170                 175

Gln Val Asn Thr Arg Glu Lys Pro Ile Thr Thr Lys Ala Thr His Gln
            180                 185                 190

Asn Lys Thr Met Gly Glu Lys Lys Pro Val Glu Asp Met Ser Thr Asp
        195                 200                 205

Glu Glu Asp Glu Thr Met Asn Ile Glu Glu Asp Val Glu Val Met
    210                 215                 220

Glu Ala Lys Leu Ser Tyr Lys Ile Asp Leu Ile His Ala Ile Val Gly
225                 230                 235                 240

Arg Asn Leu Ala Lys Asp Asn Glu Thr Lys Asp Gly Val Ser Met Asp
                245                 250                 255

Asp Lys Leu Lys Ser Val Arg Gln Gln Gly Asp Glu Leu Ile Gly Cys
            260                 265                 270

Leu Ser Glu Ile Val Ser Thr Leu Asn Arg Leu His Glu Val Pro Gln
        275                 280                 285

Glu Ile Glu
    290
```

<210> SEQ ID NO 12
<211> LENGTH: 308
<212> TYPE: PRT
<213> ORGANISM: Arabidopsis thaliana

<400> SEQUENCE: 12

Met Ala Lys Val Ser Gly Arg Ser Lys Thr Ile Val Asp Asp Glu
1               5                   10                  15

Ile Ser Asp Lys Thr Ala Ser Ala Ser Glu Ser Ala Ser Ile Ala Leu
            20                  25                  30

Thr Ser Lys Arg Lys Arg Lys Ser Pro Pro Arg Asn Ala Pro Leu Gln
            35                  40                  45

Arg Ser Pro Tyr Arg Gly Val Thr Arg Trp Thr Gly Arg Tyr Glu
    50                  55                  60

Ala His Leu Trp Asp Lys Asn Ser Trp Asn Asp Thr Gln Thr Lys Lys
65                  70                  75                  80

Gly Arg Gln Gly Ala Tyr Asp Glu Glu Glu Ala Ala Arg Ala Tyr
                85                  90                  95

Asp Leu Ala Ala Leu Lys Tyr Trp Gly Arg Asp Thr Leu Leu Asn Phe
            100                 105                 110

Pro Leu Pro Ser Tyr Asp Glu Asp Val Lys Glu Met Glu Gly Gln Ser
            115                 120                 125

Lys Glu Glu Tyr Ile Gly Ser Leu Arg Arg Lys Ser Ser Gly Phe Ser
130                 135                 140

Arg Gly Val Ser Lys Tyr Arg Gly Val Ala Arg His His His Asn Gly
145                 150                 155                 160

Arg Trp Glu Ala Arg Ile Gly Arg Val Phe Gly Asn Lys Tyr Leu Tyr
                165                 170                 175

Leu Gly Thr Tyr Ala Thr Gln Glu Glu Ala Ala Ile Ala Tyr Asp Ile
            180                 185                 190

Ala Ala Ile Glu Tyr Arg Gly Leu Asn Ala Val Thr Asn Phe Asp Val
            195                 200                 205

Ser Arg Tyr Leu Asn Pro Asn Ala Ala Asp Lys Ala Asp Ser Asp
    210                 215                 220

Ser Lys Pro Ile Arg Ser Pro Ser Arg Glu Pro Glu Ser Ser Asp Asp
225                 230                 235                 240

Asn Lys Ser Pro Lys Ser Glu Glu Val Ile Glu Pro Ser Thr Ser Pro
                245                 250                 255

Glu Val Ile Pro Thr Arg Arg Ser Phe Pro Asp Ile Gln Thr Tyr
            260                 265                 270

Phe Gly Cys Gln Asp Ser Gly Lys Leu Ala Thr Glu Glu Asp Val Ile
            275                 280                 285

Phe Asp Cys Phe Asn Ser Tyr Ile Asn Pro Gly Phe Tyr Asn Glu Phe
    290                 295                 300

Asp Tyr Gly Pro
305

<210> SEQ ID NO 13
<211> LENGTH: 303
<212> TYPE: PRT
<213> ORGANISM: Arabidopsis thaliana

<400> SEQUENCE: 13

Met Ala Lys Val Ser Gly Arg Ser Lys Lys Thr Ile Val Asp Asp Glu
1               5                   10                  15

Ile Ser Asp Lys Thr Ala Ser Ala Ser Glu Ser Ala Ser Ile Ala Leu
            20                  25                  30

Thr Ser Lys Arg Lys Arg Lys Ser Pro Pro Arg Asn Ala Pro Leu Gln
        35                  40                  45

Arg Ser Pro Tyr Arg Gly Val Thr Arg His Arg Trp Thr Gly Arg
50                  55                  60

Tyr Glu Ala His Leu Trp Asp Lys Asn Ser Trp Asn Asp Thr Gln Thr
65                  70                  75                  80

Lys Lys Gly Arg Gln Val Tyr Leu Gly Ala Tyr Asp Glu Glu Ala
            85                  90                  95

Ala Ala Arg Ala Tyr Asp Leu Ala Ala Leu Lys Tyr Trp Gly Arg Asp
            100                 105                 110

Thr Leu Leu Asn Phe Pro Leu Pro Ser Tyr Asp Glu Asp Val Lys Glu
        115                 120                 125

Met Glu Gly Gln Ser Lys Glu Glu Tyr Ile Gly Ser Leu Arg Arg Lys
130                 135                 140

Ser Ser Gly Phe Ser Arg Gly Val Ser Lys Tyr Arg Gly Val Ala Arg
145                 150                 155                 160

His His His Asn Gly Arg Trp Glu Ala Arg Ile Gly Arg Val Phe Ala
                165                 170                 175

Thr Gln Glu Glu Ala Ala Ile Ala Tyr Asp Ile Ala Ala Ile Glu Tyr
            180                 185                 190

Arg Gly Leu Asn Ala Val Thr Asn Phe Asp Val Ser Arg Tyr Leu Asn
        195                 200                 205

Pro Asn Ala Ala Ala Asp Lys Ala Asp Ser Asp Ser Lys Pro Ile Arg
210                 215                 220

Ser Pro Ser Arg Glu Pro Glu Ser Ser Asp Asn Lys Ser Pro Lys
225                 230                 235                 240

Ser Glu Glu Val Ile Glu Pro Ser Thr Ser Pro Glu Val Ile Pro Thr
            245                 250                 255

Arg Arg Ser Phe Pro Asp Asp Ile Gln Thr Tyr Phe Gly Cys Gln Asp
        260                 265                 270

Ser Gly Lys Leu Ala Thr Glu Glu Asp Val Ile Phe Asp Cys Phe Asn
    275                 280                 285

Ser Tyr Ile Asn Pro Gly Phe Tyr Asn Glu Phe Asp Tyr Gly Pro
290                 295                 300

<210> SEQ ID NO 14
<211> LENGTH: 303
<212> TYPE: PRT
<213> ORGANISM: Arabidopsis thaliana

<400> SEQUENCE: 14

Met Ala Lys Val Ser Gly Arg Ser Lys Lys Thr Ile Val Asp Asp Glu
1               5                   10                  15

Ile Ser Asp Lys Thr Ala Ser Ala Ser Glu Ser Ala Ser Ile Ala Leu
            20                  25                  30

Thr Ser Lys Arg Lys Arg Lys Ser Pro Pro Arg Asn Ala Pro Leu Gln
        35                  40                  45

Arg Ser Pro Tyr Arg Gly Val Thr Arg His Arg Trp Thr Gly Arg
50                  55                  60

```
Tyr Glu Ala His Leu Trp Asp Lys Asn Ser Trp Asn Asp Thr Gln Thr
 65                  70                  75                  80

Lys Lys Gly Arg Gln Val Tyr Leu Gly Ala Tyr Asp Glu Glu Ala
                 85                  90                  95

Ala Ala Arg Ala Tyr Asp Leu Ala Ala Leu Lys Tyr Trp Gly Arg Asp
                100                 105                 110

Thr Leu Leu Asn Phe Pro Leu Pro Ser Tyr Asp Glu Asp Val Lys Glu
            115                 120                 125

Met Glu Gly Gln Ser Lys Glu Glu Tyr Ile Gly Ser Leu Arg Arg Lys
        130                 135                 140

Ser Ser Gly Phe Ser Arg Gly Val Ser Lys Tyr Arg Gly Val Ala Arg
145                 150                 155                 160

His His His Asn Gly Arg Trp Glu Ala Arg Ile Gly Arg Val Phe Ala
                165                 170                 175

Thr Gln Glu Glu Ala Ala Ile Ala Tyr Asp Ile Ala Ala Ile Glu Tyr
            180                 185                 190

Arg Gly Leu Asn Ala Val Thr Asn Phe Asp Val Asn Arg Tyr Leu Asn
        195                 200                 205

Pro Asn Ala Ala Ala Asp Lys Ala Asp Ser Asp Ser Lys Pro Ile Arg
    210                 215                 220

Ser Pro Ser Arg Glu Pro Glu Ser Ser Asp Asp Asn Lys Ser Pro Lys
225                 230                 235                 240

Ser Glu Glu Val Ile Glu Pro Ser Thr Ser Pro Glu Val Ile Pro Thr
                245                 250                 255

Arg Arg Ser Phe Pro Asp Asp Ile Gln Thr Tyr Phe Gly Cys Gln Asp
            260                 265                 270

Ser Gly Lys Leu Ala Thr Glu Glu Asp Val Ile Phe Asp Cys Phe Asn
        275                 280                 285

Ser Tyr Ile Asn Pro Gly Phe Tyr Asn Glu Phe Asp Tyr Gly Pro
    290                 295                 300
```

<210> SEQ ID NO 15
<211> LENGTH: 1146
<212> TYPE: DNA
<213> ORGANISM: Artificial sequence
<220> FEATURE:
<223> OTHER INFORMATION: synthetic

<400> SEQUENCE: 15

```
gctccgttca caccccaat tattcgaatt ccaaccctga aaatcattgt cctcctggcg      60
acggcgtttc aatgtggtcg aaacctcgtc cacgttgttg caccggctaa ccgattcttc     120
gctgctggaa gagctcgggg ctggtggcgg cggctcggag gaccaaggga caacctggtt     180
gtctccgtcc tcctcgtcgg cggcaacctc gtcctcgctc tcatcgtagt catcctcatc     240
gtcggtgtct atgtcggtgt ctatgtcgtc gtcattgcct ccttggctct cttgaccttg     300
ttcggtggtt ccgccggcgc atctctcgca cagcgagacg tgtttccga gggcggcgcc      360 ggaggccttc acggcgtgg gcgactggca cgcgtggcag aggagcgtgc cgtgtgtct      420 ttccacgagg aagttggctc catgaacctt ggcgtcgcag tcccagcata agctagcctg     480
gtccgactcg cagaaagaag tactgcgatc gcgttaacgc tttatcacga taccttctac     540
acatatcact aacaacatca acactcatca ctctcgacga catccactcg atcactactc     600
tcacacgacc gattaactcc tcatccacgc ggccgcctgc aggagccttt ctgcgagtcg     660
gaccaggcta gcttatgctg ggactgcgac gccaaggttc atggagccaa cttcctcgtg     720
```

| | |
|---|---|
| gaaagacaca cgcgcacgct cctctgccac gcgtgccagt cgcccacgcc gtggaaggcc | 780 |
| tccggcgccg ccctcggaaa caccgtctcg ctgtgcgaga gatgcgccgg cggaaccacc | 840 |
| gaacaaggtc aagagagcca aggaggcaat gacgacgaca tagacaccga catagacacc | 900 |
| gacgatgagg atgactacga tgagagcgag gacgaggttg ccgccgacga ggaggacgga | 960 |
| gacaaccagg ttgtcccttg gtcctccgag ccgccgccac cagccccgag ctcttccagc | 1020 |
| agcgaagaat cggttagccg gtgcaacaac gtggacgagg tttcgaccac attgaaacgc | 1080 |
| cgtcgccagg aggacaatga ttttcagggt tggaattcga ataattgggg atgtgaacgg | 1140 |
| agctag | 1146 |

```
<210> SEQ ID NO 16
<211> LENGTH: 497
<212> TYPE: DNA
<213> ORGANISM: Artificial sequence
<220> FEATURE:
<223> OTHER INFORMATION: synthetic

<400> SEQUENCE: 16
```

| | |
|---|---|
| gctccgttca cacccccaat tattcgaatt ccaaccctga aaatcattgt cctcctggcg | 60 |
| acggcgtttc aatgtggtcg aaacctcgtc cacgttgttg caccggctaa ccgattcttc | 120 |
| gctgctggaa gagctcgggg ctggtggcgg cggctcggag gaccaaggga caacctggtt | 180 |
| gtctccgtcc tcctcgtcgg cggcaacctc gtcctcgctc tcatcgtagt catcctcatc | 240 |
| gtcggtgtct atgtcggtgt ctatgtcgtc gtcattgcct ccttggctct cttgaccttg | 300 |
| ttcggtggtt ccgccggcgc atctctcgca cagcgagacg tgtttccga gggcggcgcc | 360 |
| ggaggccttc acggcgtgg gcgactggca cgcgtggcag aggagcgtgc gcgtgtgtct | 420 |
| ttccacgagg aagttggctc catgaacctt ggcgtcgcag tcccagcata agctagcctg | 480 |
| gtccgactcg cagaaag | 497 |

```
<210> SEQ ID NO 17
<211> LENGTH: 150
<212> TYPE: DNA
<213> ORGANISM: Artificial sequence
<220> FEATURE:
<223> OTHER INFORMATION: synthetic

<400> SEQUENCE: 17
```

| | |
|---|---|
| aagtactgcg atcgcgttaa cgctttatca cgatacccttc taccacatat cactaacaac | 60 |
| atcaacactc atcactctcg acgacatcca ctcgatcact actctcacac gaccgattaa | 120 |
| ctcctcatcc acgcggccgc ctgcaggagc | 150 |

```
<210> SEQ ID NO 18
<211> LENGTH: 500
<212> TYPE: DNA
<213> ORGANISM: Artificial sequence
<220> FEATURE:
<223> OTHER INFORMATION: synthetic

<400> SEQUENCE: 18
```

| | |
|---|---|
| ctttctgcga gtcggaccag gctagcttat gctgggactg cgacgccaag gttcatggag | 60 |
| ccaacttcct cgtggaaaga cacacgcgca cgctcctctg ccacgcgtgc cagtcgccca | 120 |
| cgccgtggaa ggcctccggc gccgccctcg gaaacaccgt ctcgctgtgc gagagatgcg | 180 |
| ccggcggaac caccgaacaa ggtcaagaga gccaaggagg caatgacgac gacatagaca | 240 |
| ccgacataga caccgacgat gaggatgact acgatgagag cgaggacgag gttgccgccg | 300 |

```
acgaggagga cggagacaac caggttgtcc cttggtcctc cgagccgccg ccaccagccc    360
cgagctcttc cagcagcgaa gaatcggtta gccggtgcaa caacgtggac gaggtttcga    420
ccacattgaa acgccgtcgc caggaggaca atgattttca gggttggaat cgaataatt     480 ggggatgtga acggagctag                                                500
```

<210> SEQ ID NO 19
<211> LENGTH: 666
<212> TYPE: DNA
<213> ORGANISM: Glycine Max

<400> SEQUENCE: 19

```
atgaagaact gcgagttgtg caagcttccg gctcggactt tctgcgagtc ggaccaggct     60
agcttatgct gggactgcga cgccaaggtt catggagcca acttcctcgt ggaaagacac   120
acgcgcacgc tcctctgcca cgcgtgccag tcgcccacgc cgtggaaggc ctccggcgcc   180
gccctcggaa acaccgtctc gctgtgcgag agatgcgccg gcggaaccac cgaacaaggt   240
caagagagcc aaggaggcaa tgacgacgac atagacaccg acatagacac cgacgatgag   300
gatgactacg atgagagcga ggacgaggtt gccgccgacg aggaggacgg agacaaccag   360
gttgtccctt ggtcctccga gccgccgcca ccagccccga gctcttccag cagcgaagaa   420
tcggttagcc ggtgcaacaa cgtggacgag gtttcgacca cattgaaacg ccgtcgccag   480
gaggacaatg attttcaggg ttggaattcg aataattggg gatgtgaacg gagcgaagtg   540
gagagaggag gttggttggt tcggttgcgg cggagaaccg ccgatgatgt ggcggttgag   600
caacggagtg ctagagcggc gtctccagac ggttgctgtg gtgatagagc atctgaagac   660
gtttga                                                              666
```

<210> SEQ ID NO 20
<211> LENGTH: 221
<212> TYPE: PRT
<213> ORGANISM: Glycine Max

<400> SEQUENCE: 20

```
Met Lys Asn Cys Glu Leu Cys Lys Leu Pro Ala Arg Thr Phe Cys Glu
1               5                  10                  15

Ser Asp Gln Ala Ser Leu Cys Trp Asp Cys Asp Ala Lys Val His Gly
            20                  25                  30

Ala Asn Phe Leu Val Glu Arg His Thr Arg Thr Leu Leu Cys His Ala
        35                  40                  45

Cys Gln Ser Pro Thr Pro Trp Lys Ala Ser Gly Ala Ala Leu Gly Asn
    50                  55                  60

Thr Val Ser Leu Cys Glu Arg Cys Ala Gly Gly Thr Thr Glu Gln Gly
65                  70                  75                  80

Gln Glu Ser Gln Gly Gly Asn Asp Asp Asp Ile Asp Thr Asp Ile Asp
                85                  90                  95

Thr Asp Asp Glu Asp Asp Tyr Asp Glu Ser Glu Asp Glu Val Ala Ala
            100                 105                 110

Asp Glu Glu Asp Gly Asp Asn Gln Val Val Pro Trp Ser Ser Glu Pro
        115                 120                 125

Pro Pro Pro Ala Pro Ser Ser Ser Ser Glu Glu Ser Val Ser Arg
    130                 135                 140

Cys Asn Asn Val Asp Glu Val Ser Thr Thr Leu Lys Arg Arg Arg Gln
145                 150                 155                 160
```

-continued

| Glu | Asp | Asn | Asp | Phe | Gln | Gly | Trp | Asn | Ser | Asn | Asn | Trp | Gly | Cys | Glu |
| | | | | 165 | | | | | 170 | | | | | 175 | |

| Arg | Ser | Glu | Val | Glu | Arg | Gly | Gly | Trp | Leu | Val | Arg | Leu | Arg | Arg | Arg |
| | | | 180 | | | | | 185 | | | | | 190 | | |

| Thr | Ala | Asp | Asp | Val | Ala | Val | Glu | Gln | Arg | Ser | Ala | Arg | Ala | Ala | Ser |
| | | 195 | | | | | 200 | | | | | 205 | | | |

| Pro | Asp | Gly | Cys | Cys | Gly | Asp | Arg | Ala | Ser | Glu | Asp | Val |
| 210 | | | | | | 215 | | | | | 220 | |

TRANSGENIC PLANTS WITH ENHANCED TRAITS

CROSS REFERENCE TO RELATED APPLICATIONS

This application is a continuation application of U.S. application Ser. No. 15/027,821 filed Apr. 7, 2016, which is a U.S. National Stage filing under 35 U.S.C. § 371 of International Application No PCT/US2014/059261 filed Oct. 6, 2014, which claims benefit and priority to U.S. Provisional Application No. 61/932,941 filed on Jan. 29, 2014 and U.S. Provisional Application No. 61/887,552 filed on Oct. 7, 2013, which are incorporated herein by reference.

INCORPORATION OF SEQUENCE LISTING

The Sequence Listing accompanying this application is contained within the computer readable file "Sequence_Listing-P34446US03.txt" submitted electronically and contemporaneously with the filing of this application through the USPTO EFS-Web. The file is 35,053 bytes (measured in MS-Windows), was created on Aug. 29, 2019, and is incorporated herein by reference.

FIELD OF THE INVENTION

Disclosed herein are plants having enhanced traits such as increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with enhanced traits.

SUMMARY OF THE INVENTION

An aspect of this disclosure provides a plant comprising a recombinant DNA molecule comprising a polynucleotide encoding a polypeptide, wherein the nucleotide sequence of the polynucleotide is selected from the group consisting of: a) a nucleotide sequence set forth as SEQ ID NO: 1, 3, 5, 7 or 9; b) a nucleotide sequence encoding a protein having the amino acid sequence of SEQ ID NO: 2, 4, 6, 8, 10, 11, 12, 13 or 14; c) a nucleotide sequence with at least 90%, at least 91%, at least 92%, at least 93%, at least 94%, at least 95%, at least 96%, at least 97%, at least 98%, or at least 99% identity to SEQ ID NO: 1, 3, 5, 7 or 9; and d) a nucleotide sequence encoding a protein with at least 90%, at least 91%, at least 92%, at least 93%, at least 94%, at least 95%, at least 96%, at least 97%, at least 98%, or at least 99% identity to SEQ ID NO: 2, 4, 6, 8, 10, 11, 12, 13 or 14; wherein said plant has an enhanced trait as compared to a control plant, and wherein said enhanced trait is selected from the group consisting of increased yield, increased nitrogen use efficiency, and increased water use efficiency.

Another aspect of this disclosure provides a plant comprising a recombinant DNA molecule of the disclosure, wherein said plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, *Miscanthus* plant, pampas grass plant, switchgrass (*Panicum*) plant, and/or teosinte plant, or is a member of the family Alliaceae, onion plant, leek plant, garlic plant; or wherein the plant is a dicot plant or is a member of the family Musaceae, banana plant, or is a member of the family Amaranthaceae, spinach plant, quinoa plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, papaya plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, eucalyptus plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, *Capsicum* plant, tobacco plant, tomatillo plant, eggplant plant, *Atropa belladona* plant, *Datura stramonium* plant, a member of the family Vitaceae, grape plant, a member of the family Umbelliferae, carrot plant, or a member of the family Musaceae, banana plant; or wherein the plant is a member of the family Pinaceae, cedar plant, fir plant, hemlock plant, larch plant, pine plant, or spruce plant.

Another aspect of this disclosure provides a plant comprising a recombinant DNA molecule of the disclosure, wherein the recombinant DNA molecule further comprises a promoter that is operably linked to the polynucleotide encoding a polypeptide, wherein said promoter is selected from the group consisting of a constitutive, inducible, tissue specific, diurnally regulated, tissue enhanced, and cell specific promoter.

Another aspect of this disclosure provides a plant comprising a recombinant DNA molecule of the disclosure, wherein said plant is a progeny, propagule, or field crop. Such field crop is selected from the group consisting of corn, soybean, cotton, canola, rice, barley, oat, wheat, turf grass, alfalfa, sugar beet, sunflower, quinoa and sugar cane.

Another aspect of this disclosure provides a plant comprising a recombinant DNA molecule of the disclosure, wherein said plant is a progeny, propagule, or field crop. Such propagule is selected from the group consisting of a cell, pollen, ovule, flower, embryo, leaf, root, stem, shoot, meristem, grain and seed.

Another aspect of this disclosure provides a method for producing a plant comprising: introducing into a plant cell a recombinant DNA molecule comprising a polynucleotide encoding a polypeptide, wherein the nucleotide sequence of the polynucleotide is selected from the group consisting of: a) a nucleotide sequence set forth as SEQ ID NO: 1, 3, 5, 7 or 9; b) a nucleotide sequence encoding a protein having the amino acid sequence of SEQ ID NO: 2, 4, 6, 8, 10, 11, 12, 13 or 14; c) a nucleotide sequence with at least 90%, at least 91%, at least 92%, at least 93%, at least 94%, at least 95%, at least 96%, at least 97%, at least 98%, or at least 99% identity to SEQ ID NO: 1, 3, 5, 7 or 9; and d) a nucleotide sequence encoding a protein with at least 90%, at least 91%, at least 92%, at least 93%, at least 94%, at least 95%, at least 96%, at least 97%, at least 98%, at least 99% identity to SEQ ID NO: 2, 4, 6, 8, 10, 11, 12, 13 or 14; and growing a plant from said plant cell.

Another aspect of this disclosure provides a method of producing a plant comprising: introducing into a plant cell a recombinant DNA molecule of the disclosure; growing a plant from said plant cell; and selecting a plant with an enhanced trait selected from increased yield, increased nitrogen use efficiency, and increased water use efficiency as compared to a control plant.

Another aspect of this disclosure provides a method of increasing yield, increasing nitrogen use efficiency, or increasing water use efficiency in a plant comprising: producing a plant comprising a recombinant DNA of the disclosure wherein said plant has an enhanced trait selected from the group consisting of increased yield, increased nitrogen use efficiency, and increased water use efficiency as compared to a control plant; crossing said plant with itself, a second plant from the same plant line, a wild type plant, or a second plant from a different line of plants to produce a seed; growing said seed to produce a plurality of progeny plants, and selecting a progeny plant with increased yield, increased nitrogen use efficiency, or increased water use efficiency.

Another aspect of this disclosure provides a plant comprising a recombinant DNA molecule comprising a polynucleotide encoding a polypeptide, wherein the nucleotide sequence of the polynucleotide is selected from the group consisting of: a) a nucleotide sequence set forth as SEQ ID NO: 1, 3, 5, 7 or 9; b) a nucleotide sequence encoding a protein having the amino acid sequence of SEQ ID NO: 2, 4, 6, 8, 10, 11, 12, 13 or 14; c) a nucleotide sequence with at least 90%, at least 91%, at least 92%, at least 93%, at least 94%, at least 95%, at least 96%, at least 97%, at least 98%, at least 99% identity to SEQ ID NO: 1, 3, 5, 7 or 9; and d) a nucleotide sequence encoding a protein with at least 90%, at least 91%, at least 92%, at least 93%, at least 94%, at least 95%, at least 96%, at least 97%, at least 98%, at least 99% identity to SEQ ID NO: 2, 4, 6, 8, 10, 11, 12, 13 or 14, wherein said plant has at least one phenotype selected from the group consisting of anthocyanin content, biomass, canopy area, chlorophyll content, plant height, water applied, water content and water use efficiency that is altered for said plant as compared to a control plant.

In another aspect the disclosure provides a plant comprising a recombinant DNA molecule that is transcribed into a non-coding RNA molecule for suppressing expression of a target protein, wherein a) said target protein is selected from the group consisting of i) a protein comprising an amino acid sequence as set forth in SEQ ID NO:20; and ii) a protein comprising an amino acid sequence with at least 90%, at least 91%, at least 92%, at least 93%, at least 94%, at least 95%, at least 96%, at least 97%, at least 98%, or at least 99% identity to SEQ ID NO: 20; and b) said recombinant DNA molecule comprises a heterologous promoter operably linked to a suppressor element, wherein said suppressor element is an inverted repeat comprising i) a fragment of a polynucleotide sequence encoding the target protein; ii) a fragment of the polynucleotide sequence of SEQ ID NO:19; iii) the polynucleotide sequence of SEQ ID NO: 16; or iv) the polynucleotide sequence of SEQ ID NO: 15; wherein said plant exhibits an enhanced trait or an altered phenotype as compared to a control plant.

In another aspect the disclosure provides a method for producing a plant having an altered phenotype or an enhanced trait, said method comprising introducing into a plant cell a recombinant DNA molecule that is transcribed into a non-coding RNA molecule for suppressing expression of a target protein, wherein: a) said target protein is selected from the group consisting of i) a protein comprising an amino acid sequence as set forth in SEQ ID NO:20; and ii) a protein comprising an amino acid sequence with at least 90%, at least 91%, at least 92%, at least 93%, at least 94%, at least 95%, at least 96%, at least 97%, at least 98%, or at least 99% identity to SEQ ID NO: 20; and b) said recombinant DNA molecule comprises a heterologous promoter operably linked to a suppressor element, wherein said suppressor element is an inverted repeat comprising i) a fragment of a polynucleotide sequence encoding the target protein; ii) a fragment of the polynucleotide sequence of SEQ ID NO:19; iv) the polynucleotide sequence of SEQ ID NO:16; or iv) the polynucleotide sequence of SEQ ID NO: 15; and growing a plant from said cell.

DETAILED DESCRIPTION OF THE INVENTION

In the attached sequence listing:

SEQ ID NOs: 1, 3, 5, 7 and 9 are the nucleotide sequences of the coding strand of the recombinant DNA molecules imparting an enhanced trait or altered phenotype in plants, with SEQ ID NOs: 1, 3, 5, 7 and 9 each representing a coding sequence for a protein.

SEQ ID NOs: 2, 4, 6, 8 and 10 are the amino acid sequences of the cognate proteins of the DNA molecules with SEQ ID NOs: 1, 3, 5, 7 and 9.

SEQ ID NOs: 11, 12, 13 and 14 are the amino acid sequences of homologous proteins.

SEQ ID NO: 15 is the nucleotide sequence of a suppressor element in a recombinant DNA molecule imparting an enhanced trait or an altered phenotype in plants.

SEQ ID NO: 16 is the nucleotide sequence of the antisense strand in the suppressor element of SEQ ID NO: 15.

SEQ ID NO: 17 is the nucleotide sequence of the linker in the suppressor element of SEQ ID NO: 15.

SEQ ID NO: 18 is the nucleotide sequence of the sense strand in the suppressor element of SEQ ID NO: 15.

SEQ ID NO: 19 is the nucleotide sequence of a target protein the expression of which is modulated by the suppressor element of SEQ ID NO: 15.

SEQ ID NO: 20 is the amino acid sequence of the target protein.

"Modulation" of expression refers to the process of effecting either overexpression or suppression of a polynucleotide or a protein.

The term "overexpression" as used herein refers to a greater expression level of a polynucleotide or a protein in a plant, plant cell or plant tissue, compared to expression in a wild-type plant, cell or tissue, at any developmental or temporal stage for the gene. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "target protein" as used herein in the context of overexpression refers to a protein which is overexpressed; "target mRNA" refers to an mRNA which encodes and is translated to produce the target protein, which can also be overexpressed. In alternative embodiments, the target protein can effect an enhanced trait or altered phenotype directly or indirectly. In the latter case it may do so, for example, by affecting the expression, function or substrate available to one or more other proteins. In an exemplary embodiment, the target protein can bind to one or more other proteins associated with an altered phenotype or enhanced trait to enhance or inhibit their function.

Overexpression can be achieved using numerous approaches. In one embodiment, overexpression can be achieved by placing the DNA sequence encoding one or more polynucleotides or polypeptides under the control of a promoter, examples of which include but are not limited to endogenous promoters, heterologous promoters, inducible promoters and tissue specific promoters. In one exemplary embodiment, the promoter is a constitutive promoter, for example, the cauliflower mosaic virus 35S transcription initiation region. Thus, depending on the promoter used, overexpression can occur throughout a plant, in specific tissues of the plant, or in the presence or absence of different inducing or inducible agents, such as hormones or environmental signals.

Conversely, the term "suppression" as used herein refers to a lower expression level of a target polynucleotide or target protein in a plant, plant cell or plant tissue, as compared to the expression in a wild-type or control plant, cell or tissue, at any developmental or temporal stage for the gene. The term "target protein" as used in the context of suppression refers to a protein which is suppressed; similarly, "target mRNA" refers to a polynucleotide which can be suppressed or, once expressed, degraded so as to result in suppression of the target protein it encodes. In alternate non-limiting embodiments, the target protein or target polynucleotide is one the suppression of which can give rise to an enhanced trait or altered phenotype directly or indirectly. In one exemplary embodiment, the target protein is one which can indirectly increase or decrease the expression of one or more other proteins, the increased or decreased expression, respectively, of which is associated with an enhanced trait or an altered phenotype. In another exemplary embodiment, the target protein can bind to one or more other proteins associated with an altered phenotype or enhanced trait to enhance or inhibit their function and thereby effect the altered phenotype or enhanced trait indirectly.

Suppression can be applied using numerous approaches. Non limiting examples include: suppressing an endogenous gene(s) or a subset of genes in a pathway, suppressing one or more mutation that has resulted in decreased activity of a protein, suppressing the production of an inhibitory agent, to elevate, reducing or eliminating the level of substrate that an enzyme requires for activity, producing a new protein, activating a normally silent gene; or accumulating a product that does not normally increase under natural conditions.

Small RNAs that regulate protein expression include miRNAs and ta-siRNAs. A miRNA is a small (typically about 21 nucleotides) RNA that has the ability to modulate the expression of a target gene by binding to a messenger RNA encoding a target protein at specific "siRNA binding sites" to form a RNA duplex, leading to destabilization of the target protein messenger RNA or to translational inhibition of the target protein messenger RNA. SiRNAs have a well-defined structure: a short (usually 21 nucleotides) double-stranded RNA (dsRNA) with phosphorylated 5' ends and hydroxylated 3' ends with two overhanging nucleotides. The "Dicer" enzyme catalyzes production of siRNAs from long dsRNAs and small hairpin RNAs. These siRNAs are incorporated into the RNA-induced silencing complex (RISC), which targets messenger RNA to prevent translation.

Suppression of a target protein by means of such small RNAs are aspects of the invention that are conveniently illustrated by reference to use of recombinant polynucleotides encoding non-coding long double stranded RNAs that are then endogenously processed to provide siRNAs. In one embodiment, the recombinant DNA molecule comprises a suppressor element comprising inverted repeats. In one non-limiting example of this embodiment, the suppressor element is an inverted repeat comprising, in sequential order from 5' to 3', an antisense polynucleotide sequence, a linker or loop sequence and a sense polynucleotide sequence which is complimentary to the antisense sequence. In this embodiment, the sense and the antisense polynucleotides hybridize under physiological conditions to form a "hairpin" or "stem and loop" structure in which the sense and the antisense strands form a double-stranded "stem," while the loop remains in a single-stranded state. In alternate exemplary embodiments, there may be multiple pairs of sense and antisense sequences, and multiple linker sequences, arranged such that the non-coding RNA transcribed from the suppressor element forms structures exhibiting multiple stems and loops.

The sense and the antisense polynucleotide sequences are selected so as to optimize suppression of the target gene, to avoid undesirable suppression of unintended target proteins, and to avoid the formation of secondary structure by the non-coding dsRNA which would impede or prevent suppression. The exemplary embodiment described in Example 9 provides a recombinant DNA molecule having the polynucleotide sequence set forth in SEQ ID NO: 15 which is transcribed into a non-coding RNA capable of forming a hairpin structure. In this example, the sense sequence is 500 nucleotides in length, while the antisense is 497 nucleotides in length, and the linker sequence is 150 nucleotides long. Other exemplary embodiments of suppressor elements comprise sense, antisense and linker sequences having sequences and/or lengths different from those in SEQ ID NO: 15, and/or comprise multiple sense, antisense and linker sequences capable of forming multiple stem and loop structures.

In one embodiment, the disclosure provides a transgenic plant cell comprising a recombinant DNA molecule transcribed into a non-coding RNA that effects suppression of a target protein. In a further embodiment, the plant exhibits an altered phenotype. In an alternate embodiment, the plant exhibits an enhanced trait.

Therefore, in one exemplary embodiment, the disclosure provides a transgenic plant cell comprising a recombinant DNA molecule that suppresses the expression of a target polypeptide comprising the amino acid sequence of SEQ ID NO: 20 and wherein the recombinant DNA comprises a polynucleotide sequence that is a fragment of SEQ ID NO: 19. In a further exemplary embodiment the recombinant DNA molecule comprises the polynucleotide sequence set forth in SEQ ID NO: 16. In a further exemplary embodiment the recombinant DNA comprises the polynucleotide sequence of SEQ ID NO: 15. In alternate exemplary embodiments the plant exhibits increased yield, or an altered phenotype as compared to control plants when grown under non-stress conditions or under conditions of water deficit.

In a further embodiment, the disclosure provides a method of producing transgenic plants exhibiting an enhanced trait or an altered phenotype relative to a control plant, said method comprising the steps of introducing into a plant cell a recombinant DNA molecule comprising a suppressor element that is transcribed into a non-coding RNA that effects suppression of a target protein, and growing a plant from the cell.

Thus, in one exemplary embodiment, the disclosure provides a method of producing a transgenic plant exhibiting an enhanced trait or an altered phenotype relative to a control plant, said method comprising the steps of introducing into a plant cell a recombinant DNA molecule transcribed into a non-coding RNA that effects suppression of a target protein, and growing a plant from the cell, wherein said target protein comprises the amino acid sequence set forth in SEQ ID NO: 20 and the recombinant DNA molecule comprises a fragment of the polynucleotide set forth in SEQ ID NO: 19. In a further exemplary embodiment, the recombinant DNA molecule comprises the polynucleotide sequence of SEQ ID NO: 16. In a further exemplary embodiment, the recombinant DNA molecule comprises the polynucleotide of SEQ ID NO: 15.

As used herein a "plant" includes a whole plant, a transgenic plant, meristematic tissue, a shoot organ/structure (for example, leaf, stem and tuber), a root, a flower, a floral organ/structure (for example, a bract, a sepal, a petal, a stamen, a carpel, an anther and an ovule), a seed (including an embryo, endosperm, and a seed coat) and a fruit (the mature ovary), plant tissue (for example, vascular tissue, ground tissue, and the like) and a cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multi-cellular algae.

As used herein a "transgenic plant cell" means a plant cell that is transformed with a recombinant DNA, for example, by Agrobacterium-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, for example, into a transgenic plant with a recombinant DNA, or seed or pollen derived from a progeny transgenic plant.

As used herein a "control plant" means a plant that does not contain the recombinant DNA of the present disclosure that imparts an enhanced trait. A control plant is used to identify and select a transgenic plant that has an enhanced trait. A suitable control plant can be a non-transgenic plant of the parental line used to generate a transgenic plant, for example, a wild type plant devoid of a recombinant DNA. A suitable control plant can also be a transgenic plant that contains recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isogenic line.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of drought tolerance, increased water use efficiency, cold tolerance, increased nitrogen use efficiency, increased yield, and altered phenotypes as shown in Tables 4-8. In another aspect of the disclosure the trait is increased yield under non-stress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait as compared to a control plant. It is known that there can be natural variations in a modified trait. Therefore, the trait modification observed entails a change of the normal distribution and magnitude of the trait in the plants as compared to a control plant.

The present disclosure relates to a plant with improved economically important characteristics, more specifically increased yield. More specifically the present disclosure relates to a plant comprising a polynucleotide of this disclosure that encodes a polypeptide, or comprising a polynucleic acid sequence transcribed into an mRNA which effects suppression of an endogenous polypeptide, wherein the plant has increased yield as compared to a control plant. Many plants of this disclosure exhibited increased yield as compared to a control plant. In an embodiment, a plant of the present disclosure exhibited an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), seed production and more. Root development, photosynthetic efficiency, nutrient uptake, stress tolerance, early vigor, delayed senescence and functional stay green phenotypes can be important factors in determining yield. Optimizing the above mentioned factors can therefore contribute to increasing crop yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive biomass (e.g., ear biomass or ear biomass per plot), and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear, weight per kernel, ear number, fresh or dry ear biomass (weight), kernel rows per ear and kernels per row.

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kg/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure provides a method for the production of plants having increased yield; performance of the method gives plants increased yield. "Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others.

Further, increased yield can also manifest as (iii) increased total seed yield, which may result from one or more of an increase in seed biomass (seed weight) due to an increase in the seed weight on a per plant and/or on an individual seed basis an increased number of panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds.

Increased yield can also (iv) result in modified architecture, or can occur because of modified plant architecture.

Increased yield can also manifest as (v) increased harvest index, which is expressed as a ratio of the yield of harvestable parts, such as seeds, over the total biomass Increased yield can also manifest as (vi) increased kernel weight, which is extrapolated from the number of filled seeds counted and their total weight. An increased kernel weight can result from an increased seed size and/or seed weight, an increase in embryo size, increased endosperm size, alcurone and/or scutellum, or an increase with respect to other parts of the seed that result in increased kernel weight.

Increased yield can also manifest as (vii) increased ear biomass, which is the weight of the ear and can be represented on a per ear, per plant or per plot basis.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to, seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of increasing yield in a plant by crossing a plant comprising a recombinant DNA molecule of the present disclosure with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA, transgenic plants can be prepared by crossing a first plant having a recombinant DNA with a second plant lacking the DNA. For example, recombinant DNA can be introduced into a first plant line that is amenable to transformation to produce a transgenic plant which can be crossed with a second plant line to introgress the recombinant DNA into the second plant line.

A transgenic plant with a recombinant DNA comprising the polynucleotide of this disclosure provides at least one enhanced trait of increased yield, increased nitrogen use efficiency or increased water use efficiency compared to a control plant. Genetic markers associated with the recombinant DNA can be used to identify transgenic progeny that is homozygous for the desired recombinant DNA. Progeny plants carrying the recombinant DNA can be back crossed into either parental or transgenic lines multiple times, for example usually 6 to 8 generations, to produce a progeny plant with substantially the same genotype as the one original transgenic parental line. The term "progeny" denotes the offspring of any generation of a parent plant prepared by the methods of this disclosure comprising the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, re-translocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, oligonucleotide, nucleotide, or any fragment thereof. In many instances, a polynucleotide encodes a polypeptide (or protein) or a domain or fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide. A "synthetic polypeptide" is a polypeptide created by consecutive polymerization of isolated amino acid residues using methods well known in the art.

A "DNA construct" as used in the present disclosure comprises at least one expression cassette having a promoter operable in plant cells and a polynucleotide of the present disclosure encoding a protein or variant of a protein or fragment of a protein that is functionally defined to maintain activity in host cells including plant cells, plant parts, explants and plants. DNA constructs are made that contain various genetic elements necessary for the expression of noncoding and coding polynucleotides in plants. Promoters, leaders, enhancers, introns, transit or targeting or signal peptide sequences, 3' transcriptional termination regions are genetic elements that can be operably linked in a DNA construct.

In alternative embodiments, the expression cassette may comprise a polynucleotide encoding a suppression element.

Recombinant DNA constructs are assembled using methods well known to persons of ordinary skill in the art and typically comprise a promoter operably linked to DNA, the expression of which provides an enhanced agronomic trait. Other construct components can include additional regulatory elements, such as 5' leaders and introns for enhancing transcription, 3' untranslated regions (such as polyadenylation signals and sites), and DNA for transit or targeting or signal peptides.

Percent identity describes the extent to which polynucleotides or protein segments are invariant in an alignment of sequences, for example nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "functional fragment" refers to a portion of a polypeptide provided herein which retains full or partial molecular, physiological or biochemical function of the full length polypeptide. A functional fragment often contains the domain(s), such as Pfam domains, identified in the polypeptide provided in the sequence listing.

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from a common ancestral gene by speciation and encode proteins retain the same function, but do not include paralogs, for example, genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins have typically at least about 60% identity, in some instances at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, and even at least about 99.5% identity over the full length of a protein identified as being associated with imparting an enhanced trait when expressed in plant cells. In one aspect of the disclosure homolog proteins have amino acid sequences that exhibit at least about 80%, at least about 85%, at least about 90%, at least about 91%, at least about 92%, at least about 93%, at least about 94%, at least about 95%, at least about 96%, at least about 97%, at least about 98%, at least about 99%, and even at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using well-known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of the well-known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

Homologs can be identified for the polypeptide sequences provided in Table 1, using the reciprocal search process as described supra. The NCBI "blastp" program can be used for the sequence search, with E-value cutoff of 1e-4 to identify the initial significant hits. NCBI non-redundant amino-acid dataset can be used as the database of protein sequences of various organisms. Homologs with at least 95% identity over 95% of the length of the polypeptide sequences provided in Table 1 would be kept. From the sequences of the proteins identified in SEQ ID NOs: 6 and 8, the corresponding homologous protein sequences as set forth as SEQ ID NO: 11 (homolog of SEQ ID NO: 6) and SEQ ID NOs: 12, 13 and 14 (homologs of SEQ ID NO: 8), were identified for preparing additional transgenic seeds and plants with enhanced agronomic traits.

"Pfam" is a large collection of multiple sequence alignments and hidden Markov models covering many common protein families, for example, Pfam version 27.0 (March 2013) contains alignments and models for 14831 protein families. See The Pfam protein families database: M. Punta, P. C. Coggill, R. Y. Eberhardt, J. Mistry, J. Tate, C. Boursnell, N. Pang, K. Forslund, G. Ceric, J. Clements, A. Heger, L. Holm, E. L. L. Sonnhammer, S. R. Eddy, A. Bateman, R. D. Finn Nucleic Acids Research (2012) Database Issue 40:D290-D301, which is incorporated herein by reference in its entirety. The Pfam database is currently maintained and updated by the Pfam Consortium. The alignments represent some evolutionary conserved structure that has implications for protein function. Profile hidden Markov models (profile HMMs) are built from the protein family alignments and are useful for automatically recognizing that a new protein belongs to an existing protein family even if the homology by alignment appears to be low.

Protein domains are identified by querying the amino acid sequence of a protein against Hidden Markov Models, which characterize protein family domains ("Pfam domains"), using HMMER software. HMMER software is well-known and well-understood in the art, and is available from the Pfam Consortium. The HMMER software is also disclosed in United States Patent Application Publication No. US 2008/0148432 A1, which publication is incorporated herein by reference in its entirety. A protein domain meeting the gathering cutoff for the alignment of a particular Pfam domain is considered to contain the Pfam domain.

A "Pfam domain module" is a representation of Pfam domains in a protein, in order from N terminus to C terminus. In a Pfam domain module individual Pfam domains are separated by double colons "::". The order and copy number of the Pfam domains from N to C terminus are attributes of a Pfam domain module. Although the copy number of repetitive domains is important, varying copy number often enables a similar function. Thus, a Pfam domain module with multiple copies of a domain should define an equivalent Pfam domain module with variance in the number of multiple copies. A Pfam domain module is not specific for distance between adjacent domains, but contemplates natural distances and variations in distance that provide equivalent function. The Pfam database contains both narrowly- and broadly-defined domains, leading to identification of overlapping domains on some proteins. A Pfam domain module is characterized by non-overlapping domains. Where there is overlap, the domain having a function that is more closely associated with the function of the protein (based on the E value of the Pfam match) is selected.

Once one DNA is identified as encoding a protein which imparts an enhanced trait when expressed in transgenic plants, or which imparts an enhanced trait by virtue of its being suppressed, other DNA encoding proteins with the same Pfam domain module are identified by querying the amino acid sequence of protein encoded by the candidate DNA against the Hidden Markov Models which characterizes the Pfam domains using HMMER software. Candidate proteins meeting the same Pfam domain module are in the protein family and have cognate DNA that is useful in constructing recombinant DNA for the use in the plant cells of this disclosure. Hidden Markov Model databases for the use with HMMER software in identifying DNA expressing protein with a common Pfam domain module for recombinant DNA in the plant cells of this disclosure are included in the computer program listing in this application.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences may be similar overall and, in many regions, identical. Due to the degeneracy of the genetic code, differences between may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application.

Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

In one embodiment, expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252, zein Z27 as disclosed by Russell et al. (1997) *Transgenic Res.* 6(2):157-166, globulin 1 as disclosed by Belanger et al (1991) *Genetics* 129:863-872, glutelin 1 as disclosed by Russell (1997) supra, and peroxiredoxin antioxidant (Per1) as disclosed by Stacy et al. (1996) *Plant Mol Biol.* 31(6):1205-1216.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule.

As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be heterologous with respect to the transcribable polynucleotide molecule. Expression cassettes of this disclosure can also include multiple introns.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, and vacuolar sorting peptides. For description of the use of chloroplast transit peptides see U.S. Pat. Nos. 5,188,642 and 5,728,925. For a description of the transit peptide region of an *Arabidopsis* EPSPS gene, see Klee, H. J. Et al (MGG (1987) 210:437-442. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-noncoding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989.

Recombinant DNA molecules in this disclosure generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication Nos. 2002/0192813 A1; and the pea (*Pisum sativum*) ribulose biphosphate carboxylase gene (rbs 3'), and 3' elements from the genes within the host plant.

Expression cassettes of this disclosure can also contain one or more genes that encode selectable markers and confer resistance to a selective agent such as an antibiotic or an herbicide. A number of selectable marker genes are known in the art and can be used in the present disclosure. For example, selectable marker genes conferring tolerance to antibiotics like kanamycin and paromomycin (nptII), hygromycin B (aph IV), spectinomycin (aadA), US Patent Publication No. 2009/10138985A1 and gentamycin (aac3 and aacC4) or tolerance to herbicides like glyphosate (for example, 5-enolpyruvylshikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761, 373; 5,633,437; 6,613,963; 5,013,659; 5,141,870; 5,378, 824; 5,605,011)), bialaphos or phosphinothricin or derivatives (e.g., phosphinothricin acetyltransferase (bar)

tolerance to phosphinothricin or glufosinate (U.S. Pat. Nos. 5,646,024; 5,561,236; 5,276,268; 5,637,489; 5,273,894); dicamba (dicamba monooxygenase, Patent Application Publication No. US2003/0115626A1), or sethoxydim (modified acetyl-coenzyme A carboxylase for conferring tolerance to cyclohexanedione (sethoxydim)), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR termination signal, for expression in an appropriate host cell. It also typically comprises sequences required for proper translation of the polynucleotide or transgene.

As used herein, the term "transgene" refers to a polynucleotide molecule artificially incorporated into a host cell's genome. Such a transgene can be heterologous to the host cell. The expression cassette comprising the nucleotide sequence of interest can be chimeric, meaning that at least one of its components is heterologous with respect to at least one of its other components. As used heroin the term "chimeric" refers to a DNA molecule that is created from two or more genetically diverse sources, for example a first molecule from one gene or organism and a second molecule from another gene or organism.

As used herein "operably linked" means the association of two or more DNA fragments in a recombinant DNA molecule so that the function of one, for example, protein-encoding DNA, is controlled by the other, for example, a promoter.

As used herein "expressed" means produced, for example, a protein is expressed in a plant cell when its cognate DNA is transcribed to mRNA that is translated to the protein. An "expressed" protein can also include its truncated version (for example, N-terminal truncated, C-terminal truncated or internal truncated) as long as the truncated version maintains the same or similar functionality as the full length version.

Transgenic plants can comprise a stack of one or more polynucleotides disclosed herein resulting in the production of multiple polypeptide sequences. Transgenic plants comprising stacks of polynucleotides can be obtained by either traditional breeding methods or through genetic engineering methods or by both. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication No. US 2003/0083480 A1 also for imparting glyphosate tolerance; dicamba monooxygenase disclosed in US Patent Application Publication No. US 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance as disclosed in U.S. Pat. No. 7,112,665; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication No. US 2002/0112260. Molecules and methods for imparting insect/nematode/virus resistance are disclosed in U.S. Pat. Nos. 5,250,515; 5,880,275; 6,506,599; 5,986,175 and US Patent Application Publication No. US 2003/0150017 A1.

Plant Cell Transformation Methods

Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), and US Patent Application Publication Nos. US 2004/0087030 A1 (cotton), and US 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance or pest resistance or enhanced water use efficiency, to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application using a selective agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 micro-einsteins $m^2$ $s^1$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an enhanced agronomic trait.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of protein-encoding DNA ("genes") as recombinant DNA for production of transgenic plants with enhanced traits, the elements of Table 1 are described by reference to:

"Gene (NUC) SEQ ID NO" which identifies a DNA sequence.

"Gene (PEP) SEQ ID NO" which identifies an amino acid sequence.

"Gene ID" which refers to an arbitrary identifier.

"Protein Name" which is a common name for protein encoded by the recombinant DNA.

TABLE 1

| Gene (NUC) SEQ ID NO | Gene (PEP) SEQ ID NO | Gene ID | Protein Name |
|---|---|---|---|
| 1 | 2 | TRDX3M-1 | zinc finger (C3HC4-type) |
| 3 | 4 | TRDX3M-2 | putative sequence-specific DNA binding transcription factor |
| 5 | 6 | TRDX3M-3 | putative sequence-specific DNA binding transcription factor |
| 7 | 8 | TRDX3M-4 | putative ovule development protein containing AP2 (apetella 2) domain |
| 9 | 10 | TRDX3M-5 | protein containing Zinc finger, C2H2 type domain |

In an alternate embodiment of the disclosure, Table 2 provides a suppression element as recombinant DNA for production of transgenic plants with enhanced traits. The element of Table 2 is described by reference to:

"Suppression Element (NUC) SEQ ID NO:" which identifies the suppressor element sequence.

"Suppression Element ID", which refers to an identifier.

"Target Protein (NUC) SEQ ID NO:" which identifies the target gene nucleotide sequence for suppression.

"Target Protein (PEP) SEQ ED NO:" which identifies the amino acid sequence of the target gene.

"Target Protein Name" which is a common name for the protein encoded by the target gene DNA.

TABLE 2

| Suppression Element (NUC) SEQ ID NO: | Suppression Element ID | Target Protein (NUC) SEQ ID NO: | Target Protein (PEP) SEQ ID NO: | Target Protein Name |
|---|---|---|---|---|
| 15 | TRDX3M-6 | 19 | 20 | B-Box containing protein |

Selection Methods For Transgenic Plants With Enhanced Traits

Within a population of transgenic plants each regenerated from a plant cell with recombinant DNA many plants that survive to fertile transgenic plants that produce seeds and progeny plants will not exhibit an enhanced agronomic trait. Selection from the population is necessary to identify one or more transgenic plants with an enhanced trait. Transgenic plants having enhanced traits are selected from populations of plants regenerated or derived from plant cells transformed as described herein by evaluating the plants in a variety of assays to detect an enhanced trait, for example, increased water use efficiency or drought tolerance, enhanced high temperature or cold tolerance, increased yield, increased nitrogen use efficiency, enhanced seed composition such as enhanced seed protein and enhanced seed oil. These assays can take many forms including, but not limited to, direct screening for the trait in a greenhouse or field trial or by screening for a surrogate trait. Such analyses can be directed to detecting changes in the chemical composition, biomass, physiological property, or morphology of the plant.

Changes in chemical compositions such as nutritional composition of grain can be detected by analysis of the seed composition and content of protein, free amino acids, oil, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots.

Other properties useful for selection of transgenic plants include days to pollen shed, days to silking, leaf extension rate, chlorophyll content, leaf temperature, stand, seedling vigor, internode length, plant height, leaf number, leaf area, tillering, brace roots, stay green or delayed senescence, stalk lodging, root lodging, plant health, bareness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density, ear biomass and physical grain quality.

Assays for screening for a desired trait are readily designed by those practicing in the art. The following illustrates screening assays for corn traits using hybrid corn plants. The assays can be readily adapted for screening other plants such as canola, wheat, cotton and soybean either as hybrids or inbreds.

Transgenic corn plants having increased nitrogen use efficiency are identified by screening transgenic plants in the field under the same and sufficient amount of nitrogen supply as compared to control plants, where such plants provide higher yield as compared to control plants. Transgenic corn plants having increased nitrogen use efficiency can be identified where such plants provide the same or similar yield as compared to control plants under the same nitrogen limiting conditions. For example, transgenic corn plants are shown to have increased nitrogen use efficiency compared to control plants in Table 9.

Transgenic corn plants having increased yield are identified by screening progenies of the transgenic plants over multiple locations for several years with plants grown under optimal production management practices and maximum weed and pest control. Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and water quenching on the 5th day of the cycle. The primary phenotypes analyzed by the selection method are the changes in plant growth rate as determined by height and biomass during a vegetative drought treatment.

Increased water use efficiency is indicated by increased yield, improved relative water content, enhanced leaf water potential, increased biomass, enhanced leaf extension rates, and improved fiber parameters.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, quinoa and sugar cane plants.

The following examples are included to demonstrate aspects of the disclosure. Those of skill in the art should, in light of the present disclosure, appreciate that many changes can be made in the specific aspects which are disclosed and still obtain a like or similar results without departing from the spirit and scope of the disclosure.

Example 1

Corn Transformation

This example illustrates exemplary plant transformation methods useful in producing a transgenic corn plant cell, plant, and seed having altered phenotypes as shown in Tables 4-6, or an enhanced trait, for example, increased nitrogen use efficiency, increased yield and/or increased water use efficiency or drought tolerance as shown in Tables 9, 10 and 12.

For *Agrobacterium*-mediated transformation of corn embryo cells, corn plants were grown in the greenhouse and ears were harvested when the embryos were 1.5 to 2.0 mm in length. Ears were surface-sterilized by spraying or soaking the ears in 80% ethanol, followed by air drying. Immature embryos were isolated from individual kernels on surface-sterilized ears. Shortly after excision, immature maize embryos were inoculated with overnight grown *Agrobacterium* cells, and incubated at room temperature with *Agrobacterium* for 5-20 minutes. Inoculated immature embryos were then co-cultured with *Agrobacterium* for 1 to 3 days at 23° C. in the dark. Co-cultured embryos were transferred to selection media and cultured for approximately two weeks to allow embryogenic callus to develop. Embryogenic calli were transferred to culture medium containing glyphosate and subcultured at about two week intervals. Transformed plant cells were recovered 6 to 8 weeks after initiation of selection.

For *Agrobacterium*-mediated transformation of maize callus, immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants individual transgenic calli resulting from transformation and selection were placed on media to initiate shoot and root development into plantlets. Plantlets were transferred to potting soil for initial growth in a growth chamber at 26° C. followed by a mist bench before transplanting to 5 inch pots where plants were grown to maturity. The regenerated plants were self-fertilized and seeds were harvested for use in one or more methods to select seeds, seedlings or progeny second generation transgenic plants (R2 plants) or hybrids, for example, by selecting transgenic plants exhibiting an enhanced trait as compared to a control plant.

The above process can be repeated to produce multiple events of transgenic corn plants from cells that were transformed with recombinant DNA from the genes identified in Table 1. Progeny transgenic plants and seeds of the transformed plants were screened for the presence and single copy of the inserted gene, for altered phenotypes as shown in Tables 4, 5 and 6 (see Example 3 below), and for enhanced traits, for example, increased nitrogen use efficiency, increased yield and increased water use efficiency as shown in Tables 9, 10 and 12, respectively (see Examples 4, 5 and 6 below). From each group of multiple events of transgenic plants with a specific recombinant DNA from Table 1, the event(s) that showed altered phenotypes and/or increased nitrogen use efficiency, increased yield or increased water use efficiency or drought tolerance were identified.

Example 2

Soybean Transformation

This example illustrates plant transformation methods useful in producing a transgenic soybean plant cell, seed, and plant having altered phenotypes as shown in Tables 7 and 8, and/or one or more enhanced traits, for example, increased yield as shown in Table 11.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with, for example, recombinant DNA that encodes the suppression element shown in Table 2. Progeny transgenic plants and seed of the transformed plant cells were screened for the presence and single copy of the inserted suppression element, for altered phenotypes, and/or for one or more enhanced phenotypes, for example increased yield and increased water use efficiency as shown in Tables 7, 8 and 11 (see Examples 3 and 4) below.

Example 3

Identification of Altered Phenotypes in Automated Greenhouse

This example illustrates screening and identification of transgenic plants for altered phenotypes in an automated greenhouse (AGH). The apparatus and the methods for automated phenotypic screening of plants are disclosed in US Patent publication No. US 20110135161 (filed on Nov. 10, 2010), which is incorporated by reference herein in its entirety.

Screening and Identification of Transgenic Corn Plants For Altered Phenotypes.

Corn plants were tested in 3 screens in AGH under different conditions including non-stress, nitrogen deficit and water deficit stress conditions. All screens began with a non-stress condition during day 0-5 germination phase, after which the plants were grown for 22 days under screen specific conditions. The conditions for both the non-stress and specific screens are shown in Table 3 below.

Water deficit is defined as a specific Volumetric Water Content (VWC) that is lower than the VWC of non-stress plant. For example, a non-stressed plant might be maintained at 55% VWC and water-deficit assay might be defined around 30% VWC as shown in Table 3. Data were collected using visible light and hyperspectral imaging as well as direct measurement of pot weight and amount of water and nutrient applied to individual plants on a daily basis.

Up to eight parameters were measured for each screen. The visible light color imaging based measurements are: biomass, canopy area and plant height. Biomass (B) is defined as estimated shoot fresh weight (g) of the plant obtained from images acquired from multiple angles of view. Canopy Area (Can) is defined as area of leaf as seen in top-down image (mm$^2$). Plant Height (H) refers to the distance from the top of the pot to the highest point of the plant derived from side image (mm). Anthocyanin score, chlorophyll score and water content score are hyperspectral imaging based parameters. Anthocyanin Score (An) is an estimate of anthocyanin content in the leaf canopy obtained from a top-down hyperspectral image. Chlorophyll Score (Chl) is a measurement of chlorophyll content in the leaf canopy obtained from a top-down hyperspectral image. Water Content Score (WC) is a measurement of water in the leaf canopy obtained from a top-down hyperspectral image. Water Use Efficiency (WUE) is derived from the grams of plant biomass per liter of water added. Water Applied (WA) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Table 4, Table 5 and Table 6 are summaries of transgenic corn plants comprising the disclosed recombinant DNA molecules with altered phenotypes under non-stress, nitrogen deficit and water deficit conditions, respectively.

"+" denotes an increase in the tested parameter at p≤0.1; whereas "−" denotes a decrease in the tested parameter at p≤0.1. The numbers in parenthesis show penetrance of the altered phenotypes, where the denominators represent total number of transgenic events tested for a given parameter in a specific screen, and the numerators represent the number of events showing a particular altered phenotype. For example, 5 transgenic plants were screened for chlorophyll content in the non-stress screen for TRDX3M-1 and 2 of the 5 plants tested showed increased chlorophyll at p≤0.1.

TABLE 3

Description of the 3 AGH screens

| Screen | Description | Germination phase (5 days) | Screen specific phase (22 days) |
|---|---|---|---|
| Non-stress | well watered sufficient nitrogen | 55% VWC water | 55% VWC 8 mM nitrogen |
| Water deficit | limited watered sufficient nitrogen | 55% VWC water | 30% VWC 8 mM nitrogen |
| Nitrogen deficit | well watered low nitrogen | 55% VWC water | 55% VWC 2 mM nitrogen |

TABLE 4

Summary of transgenic corn plants with altered phenotypes in AGH non-stress screens

| Gene_ID | An | B | Can | Chl | H | WA | WC | WUE |
|---|---|---|---|---|---|---|---|---|
| TRDX3M-1 | — | — | +2/5 | +1/5 | +1/5 | +1/5 | — | — |
| TRDX3M-2 | — | +1/5 | — | +2/5 | — | −1/5 | — | +2/5 |
| TRDX3M-3 | — | — | +1/5 | −1/5 | — | −3/5 | — | — |
| TRDX3M-4 | — | — | — | +1/4 | +2/4 | +1/4 | — | — |
| TRDX3M-5 | — | −2/5 | −3/5 | — | −2/5 | −2/5 | — | −2/5 |

TABLE 5

Summary of transgenic corn plants with altered phenotypes in AGH nitrogen-deficit screens

| Gene_ID | An | B | Can | Chl | H | WA | WC | WUE |
|---|---|---|---|---|---|---|---|---|
| TRDX3M-1 | — | −2/5 | −1/5 | — | +1/5 | −1/5 | +1/5 | −2/5 |
| TRDX3M-2 | — | — | +1/5 | — | +1/5 | — | −2/5 | — |
| TRDX3M-3 | +1/5 | — | +1/5 | −1/5 | — | +1/5 | — | — |
| TRDX3M-4 | | | | | | | | |
| Trial 1 | +1/5 | −1/5 | −1/5 | — | −3/5 | — | — | 1/5 |
| Trial 2 | — | −3/3 | −3/3 | +1/3 | — | −3/3 | — | −3/3 |
| Trial 3 | −1/3 | −1/3 | — | — | −1/3 | — | +1/3 | — |
| TRDX3M-5 | +1/5 | — | +1/5 | +3/5 | −1/5 | +1/5 | −2/5 | — |

TABLE 6

Summary of transgenic corn plants with altered phenotypes in AGH water-deficit screens

| Gene_ID | An | B | Can | Chl | H | WA | WC | WUE |
|---|---|---|---|---|---|---|---|---|
| TRDX3M-1 | −1/5 | +1/5 | — | — | — | — | — | +3/5 |
| TRDX3M-2 | +1/5 | — | — | — | −1/5 | +1/5 | — | +1/5 |
| TRDX3M-3 | — | — | — | −1/5 | −1/5 | +2/5 | — | −1/5 |
| TRDX3M-4 | −1/5 | −2/5 | — | −1/5 | — | −1/5 | — | — |
| TRDX3M-5 | — | −2/5 | −2/5 | −2/5 | −1/5 | −3/5 | −1/5 | — |

Screening and Identification of Transgenic Soybean Plants For Altered Phenotypes Soybean plants were tested in 2 screens in AGH under non-stress and water deficit stress conditions. For non-stress screen, the plants were kept under constant VWC of 55% throughout the screen length of 27 days. For water deficit screen, the VWC was kept at 55% for the first 12 days after sowing, followed by gradual dry down at a rate of 0.025 VWC per day, followed by water recovery to 55% VWC at 25 days after sowing.

Water deficit is defined as a specific Volumetric Water Content (VWC) that is lower than the VWC of non-stress plant. For example, a non-stressed plant might be maintained at 55% VWC and water-deficit assay might be defined around 30% VWC as shown in Table 3 in Example 3 above. Data were collected using visible light and hyperspectral imaging as well as direct measurement of pot weight and amount of water and nutrient applied to individual plants on a daily basis.

Eight parameters were measured for each screen. The visible light color imaging based measurements are: biomass, canopy area and plant height, Biomass (B) is defined as estimated shoot fresh weight (g) of the plant obtained from images acquired from multiple angles of view. Canopy Area (Can) is defined as area of leaf as seen in top-down image (mm$^2$). Plant Height (H) refers to the distance from the top of the pot to the highest point of the plant derived from side image (mm). The hyperspectral imaging based parameters are: anthocyanin score, chlorophyll score and water content score. Anthocyanin Score (An) is an estimate of anthocyanin content in the leaf canopy obtained from a top-down hyperspectral image. Chlorophyll Score (Chl) is a measurement of chlorophyll content in the leaf canopy obtained from a top-down hyperspectral image. Water Content Score (WC) is a measurement of water in the leaf canopy obtained from a top-down hyperspectral image. Water Use Efficiency (WUE) is derived from the grams of plant biomass per liter of water added. Water Applied (WA) is a direct measurement of water added to a pot (pot with no hole) during the course of an experiment.

These physiological screen runs were set up so that tested transgenic lines were compared to a control line. The collected data were analyzed against the control using % delta and/or certain p-value cutoff. Table 7 and Table 8 are summaries of transgenic soybean plants comprising the disclosed recombinant DNA molecules with altered phenotypes.

TABLE 7

Summary of transgenic soybean plants with altered phenotypes in AGH non-stress screens

| | Non-stress | | | | | | |
|---|---|---|---|---|---|---|---|
| Gene_ID | An | B | Can | Chl | H | WA | WC | WUE |
| TRDX3M-6 | — | −2/5 | −1/5 | −1/5 | −3/5 | −2/5 | — | — |

TABLE 8

Summary of transgenic soybean plants with altered phenotypes in AGH water deficit screens

| | Non-stress | | | | | | |
|---|---|---|---|---|---|---|---|
| Gene_ID | An | B | Can | Chl | H | WA | WC | WUE |
| TRDX3M-6 | — | −2/5 | −3/5 | −1/5 | −2/5 | −3/5 | — | −1/5 |

"+" denotes an increase in the tested parameter at $p \leq 0.1$; whereas "−" denotes a decrease in the tested parameter at $p \leq 0.1$. The numbers in parenthesis show penetrance of the altered phenotypes, where the denominators represent total number of transgenic plants tested for a given parameter in a specific screen, and the numerators represent the number of transgenic plants showing a particular phenotype. For example, 5 transgenic plants were screened for biomass in the non-stress screen for TRDX3M-6. Of the 5 tested, 2 showed a decrease in biomass at $p \leq 0.1$.

Example 4

Phenotypic Evaluation of Transgenic Corn Plants For Increased Nitrogen Use Efficiency Corn nitrogen field efficacy trials were conducted to identify genes that can improve nitrogen use efficiency under nitrogen limiting conditions leading to increased yield performance as compared to non transgenic controls. A yield increase in corn can be manifested as one or more of the following: an increase in the number of ears per plant, an increase in the number of rows, number of kernels per row, kernel weight, thousand kernel weight, fresh or dry ear length/diameter/biomass (weight), increase in the seed filling rate (which is the number of filled seeds divided by the total number of seeds and multiplied by 100), among others. For the Nitrogen field trial results shown in Table 9, each field was planted under nitrogen limiting condition (60 lbs/acre) and the corn ear weight or yield was compared to control plants to measure the yield increases.

Table 9 provides a list of protein-encoding DNA or polynucleotide sequences ("genes") provided as recombinant DNA for producing transgenic corn plants with increased nitrogen use efficiency as compared to a control plant. Polynucleotide sequences in constructs with at least one event showing significant yield or ear weight increase across multiple locations at $p \leq 0.2$ are included. The elements of Table 9 are described by reference to:

"Gene (NUC) SEQ ID NO:" which identifies a nucleotide sequence.

"Gene (PEP) SEQ ID NO:" which identifies an amino acid sequence.

"Gene identifier" which refers to all arbitrary identifier.

"NUE results" which refers to the sequence in a construct with at least one event showing significant yield increase at $p \leq 0.2$ across locations. The first number refers to the number of events with significant yield or ear weight increase, whereas the second number refers to the total number of events tested for each construct.

TABLE 9

Recombinant DNA for increased nitrogen use efficiency in corn

| Gene (NUC) SEQ ID NO: | Gene (PEP) SEQ ID NO: | Gene Identifier | NUE Results |
|---|---|---|---|
| 1 | 2 | TRDX3M-1 | 5/16 |
| 5 | 6 | TRDX3M-3 | 1/12 |
| 7 | 8 | TRDX3M-4 | 1/15 |

Example 5

Phenotypic Evaluation of Transgenic Plants For Increased Yield

This example illustrates selection and identification of transgenic plants for increased yield in monocotyledonous plants with a primary example presented for corn in Table 10. Polynucleotide sequences in constructs with at least one event that resulted in significant yield increase across locations at $p \leq 0.2$ are included Selection of Transgenic Plants With Enhanced Agronomic Trait(s): Increased Yield Effective selection of increased and/or enhanced yielding transgenic plants uses hybrid progenies of the transgenic plants for corn or soybean, or inbred progenies of transgenic plants such as corn or soybean over multiple locations with plants grown under optimal production management practices. An exemplary target for improved yield is a 2% to 10% increase in yield as compared to yield produced by plants grown from seed of a control plant. Selection methods can be applied in multiple and diverse geographic locations, for example up to 16 or more locations, over one or more planting seasons, for example at least two planting seasons, to statistically distinguish yield improvement from natural environmental effects.

Increased Yield in Corn

Table 10 provides a list of protein encoding DNA or polynucleotide sequences ("genes") in the production of transgenic corn plants with increased yield as compared to a control plant The elements of Table 10 are described by reference to:

"Gene (NUC) SEQ ID NO:" which identifies a nucleotide sequence.

"Gene (PEP) SEQ ID NO:" which identifies an amino acid sequence.

"Gene identifier" which refers to an arbitrary identifier.

"Broad acre yield results" refers to the sequence in a construct with at least one event showing significant yield increase at p≤0.2 across locations. The first number refers to the number of events with significant yield increase, whereas the second number refers to the total number of events tested for each sequence in a construct.

TABLE 10

Recombinant DNA for increased yield in corn

| Gene (NUC) SEQ ID NO: | Gene (PEP) SEQ ID NO: | Gene Identifier | Broad Acre Yield Results |
|---|---|---|---|
| 1 | 2 | TRDX3M-1 | 5/14 |
| 5 | 6 | TRDX3M-3 | 6/34 |
| 7 | 8 | TRDX3M-4 | 1/10 |
| 9 | 10 | TRDX3M-5 | 1/21 |

Increased Yield in Soybean

This example illustrates selection and identification of transgenic plants for increased yield in dicotyledonous plants with a primary example presented Table 11 below. Polynucleotide sequences in constructs with at least one event that resulted in significant yield increase across locations at p≤0.2 are included.

A yield increase in soybean can be manifested as one or more of the following: an increase in pods per plant, pods per acre, seeds per plant, seeds per pod, weight per seed, weight per pod, pods per node, number of nodes, and the number of internodes per plant.

Table 11 provides a suppressor element as a recombinant DNA used in the production of transgenic soybean plants with increased yield as compared to a control plant. The elements of Table 11 are described by reference to:

"Suppression Element (NUC) SEQ ID NO:" which identifies the suppressor element.

"Suppression Element ID", which refers to an identifier.

"Target Gene (NUC) SEQ ID NO:" which identifies the target gene nucleotide sequence for suppression.

"Target Gene (PEP) SEQ ID NO: which identifies the amino acid sequence of the target protein.

"Broad acre yield results" which refers to the sequence in a construct with at least one event showing significant yield increase at p≤0.2 across locations. The first number refers to the number of events with significant yield increase, whereas the second number refers to the total number of events tested for each sequence in a construct. As indicated in Table 11, suppressor element TRDX3M-6 was tested in six events and 1 significantly positive event was identified.

TABLE 11

Recombinant DNA for suppression of target genes for increased yield in soybean

| Suppression Element (NUC) SEQ ID NO: | Target Protein (NUC) SEQ ID NO: | Target Protein (PEP) SEQ ID NO: | Suppression Element Identifier | Broad Acre Yield Results |
|---|---|---|---|---|
| 15 | 19 | 20 | TRDX3M-6 | 1/11 |

Example 6

Phenotypic Evaluation of Corn For Increased Water Use Efficiency

Corn field trials were conducted to identify genes that can improve water use efficiency under water limiting conditions leading to increased yield performance as compared to non transgenic controls. A yield increase in corn can be manifested as one or more of the following: an increase in the number of ears per plant, an increase in the number of rows, number of kernels per row, kernel weight, thousand kernel weight, fresh or dry ear length/diameter/biomass (weight), increase in the seed filling rate (which is the number of filled seeds divided by the total number of seeds and multiplied by 100), among others. The water use efficiency trials for results shown in Table 12 were conducted under managed water limiting conditions, and the corn ear weight or yield was compared to control plants to measure the yield increases.

Table 12 provides a list of protein encoding DNA or polynucleotide sequences ("genes") for producing transgenic corn plant with increased water use efficiency as compared to a control plant. Polynucleotide sequences in constructs with at least one event showing significant yield or ear weight increase across multiple locations at p≤0.2 are included. The elements of Table 12 are described by reference to:

"(NUC) SEQ ID NO:" which identifies a nucleotide sequence.

"(PEP) SEQ ID NO:" which identifies an amino acid sequence.

"Gene identifier" which refers to an arbitrary identifier.

"WUE results" which refers to the sequence in a construct with at least one event showing significant yield increase at p≤0.2 across locations. The first number refers to the number of events with significant yield or ear weight increase, whereas the second number refers to the total number of events tested for each sequence in the construct.

TABLE 12

Corn water use efficiency

| (NUC) SEQ ID NO: | (PEP) SEQ ID NO: | Gene Identifier | WUE Results |
|---|---|---|---|
| 3 | 4 | TRDX3M-2 | 3/10 |
| 5 | 6 | TRDX3M-3 | 3/12 |
| 7 | 8 | TRDX3M-4 | 2/9 |

Example 7

Homolog Identification

This example illustrates the identification of homologs of proteins encoded by the DNA identified in Table 1 which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided in Table 1 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp" program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core list, otherwise it is deemed not a likely ortholog and there is no further search of sequences in the Hit List for the same organism. Homologs with at least 95% identity over 95% of the length of the polypeptide sequences provided in Table 1 are reported below in Table 13 with the SEQ ID NO of the original query sequence and the identified homologs.

TABLE 13

Protein sequences and their homologs

| Query GENE ID | Query Polypeptide SEQ ID NO | Homolog Polypeptide SEQ ID NO | Homolog Gene Name |
|---|---|---|---|
| TRDX3M-3 | 6 | 11 | Putative sequence-specific DNA binding transcription factor |
| TRDX3M-4 | 8 | 12 | APETALA2 and EREBP (ethylene responsive element binding protein) |
| TRDX3M-4 | 8 | 13 | AP2-like ethylene-responsive transcription factor |
| TRDX3M-4 | 8 | 14 | putative AP2 domain transcription factor |

Example 8

Identification of Protein Domains and Domain Modules by Pfam Analysis

This example illustrates the identification of domain and domain module by Pfam analysis.

The amino acid sequences of the expressed proteins that are shown to be associated with an enhanced trait were analyzed for Pfam protein family against the current Pfam collection of multiple sequence alignments and hidden Markov models using the HMMER software and Pfam databases (version 27.0). The Pfam protein domains and modules for the proteins of SEQ ID NOs: 2, 4, 6, 8 and 10 are shown in Tables 14, 15 and 16. The Hidden Markov model databases for the identified patent families are also available from the Pfam consortium (ftp.sanger.ac.uk/pub/databases/Pfam/) allowing identification of other homologous proteins and their cognate encoding DNA to enable the full breadth of the invention for a person of ordinary skill in the art. Certain proteins are identified by a single Pfam domain and others by multiple Pfam domains. The function of the identified Pfam domains in proteins providing an enhanced trait in plants was verified by searching identified homologs for the conservation of the identified Pfam domains. The score value for the identified Pfam domains in sequences from Table 1 and the gathering score value for the Pfam domain between a protein from Table 1 and its identified homologs are reported below in Table 16.

TABLE 14

| PEP SEQ ID NO | Pfam domain name | Begin | Stop | Hmm Score | E-value |
|---|---|---|---|---|---|
| 2 | PepSY_TM_2 | 29 | 60 | 13.0 | 6.40E−05 |
| 2 | zf-RING_2 | 110 | 153 | 61.9 | 2.60E−20 |
| 4 | Lung_7-TM_R | 24 | 64 | 13.0 | 3.40E−05 |
| 4 | zf-RING_2 | 110 | 153 | 55.2 | 4.10E−18 |
| 6 | Myb_DNA-bind_4 | 18 | 91 | 35.5 | 2.00E−12 |
| 8 | AP2 | 51 | 110 | 52.3 | 3.00E−18 |
| 8 | AP2 | 153 | 204 | 52.5 | 2.50E−18 |
| 10 | zf-C2H2_4 | 69 | 81 | 2.2 | 0.073 |
| 10 | Thrombin_light | 208 | 227 | 11.3 | 5.30E−05 |
| 10 | zf-C2H2_4 | 243 | 265 | 16.0 | 0.073 |

TABLE 15

| PEP SEQ ID NO | Pfam Domain Module | Position |
|---|---|---|
| 2 | PepSY_TM_2::zf-RING_2 | 29-60::10-153 |
| 4 | Lung_7-TM_R::zf-RING_2 | 24-64::110-153 |
| 6 | Myb_DNA-bind_4 | 18-91 |
| 8 | AP2::AP2 | 51-110, 153-204 |
| 10 | zf-C2H2_4::Thrombin_light::zf-C2H2_4 | 69-81::208-227::243-265 |

TABLE 16

| Pfam domain name | Accession number | Gathering cutoff | Domain description |
|---|---|---|---|
| AP2::AP2 | PF00847 | 20.5 | AP2 domain |
| Lung_7-TM_R | PF06814 | 25.2 | Lung seven transmembrane receptor |
| Myb_DNA-bind_4 | PF13837 | 27.0 | Myb/SANT-like DNA-binding domain |
| PepSY_TM_2 | PF13703 | 30.0 | PepSY-associated TM helix |
| Thrombin_light | PF09396 | 20.6 | Thrombin light chain |
| zf-RING_2 | PF13703 | 30.0 | Ring finger domain |
| zf-C2H2_4 | PF13894 | 9.0 | C2H2-type zinc finger |

Example 9

Recombinant DNA Molecules Comprising Suppression Elements For Producing Plants Exhibiting Altered Phenotypes or Enhanced Traits In an exemplary embodiment of the disclosure, transgenic soybean plants having altered phenotypes and enhanced yield were produced by transforming soybean cells with the recombinant DNA molecule set forth in SEQ ID NO: 15 and producing plants from the transformed cells using the methods described infra.

The recombinant DNA molecule of SEQ ID NO: 15 was constructed by linking, in 5' to 3' order, an antisense strand polynucleotide having the polynucleotide sequence set forth in SEQ ID NO:16 and complementary to nucleotides 38 through 534 of SEQ ID NO:19 except that a glycine residue replaced an alanine residue at position 522 of SEQ ID NO:16; a linker polynucleotide having the polynucleotide sequence set forth in SEQ ID NO:17; and a sense strand polynucleotide having the polynucleotide sequence set forth in SEQ ID NO:18 which is identical to nucleotides 38 to 538 of SEQ ID NO:19. Transcription of the recombinant DNA yields a non-coding RNA which, upon hybridization of the sense and antisense strands, forms a "stern and loop" structure with the single nucleotide noted above and mismatch and a three nucleotide overhang at the 3' end.

In other exemplary embodiments, recombinant molecules capable of suppressing expression of a target gene are similarly constructed. The location of the fragment is chosen so as to avoid undesirable effects such as silencing of unintended target proteins.

I claim:

1. A plant or plant part thereof, comprising a recombinant DNA molecule comprising a polynucleotide encoding a polypeptide with at least 95% identity to SEQ ID NO: 6 or 11, wherein said polypeptide comprises a Myb-domain; wherein said plant has an enhanced trait as compared to a control plant selected from the group consisting of increased yield under non-stress conditions, increased yield under water deficit stress, and increased water use efficiency; and wherein said plant is selected from the group consisting of corn and soybean.

2. The plant or plant part thereof of claim 1, wherein the recombinant DNA molecule further comprises a promoter that is operably linked to the polynucleotide encoding a polypeptide, wherein said promoter is selected from the group consisting of a constitutive, inducible, tissue specific, diurnally regulated, tissue enhanced, and cell specific promoter.

3. The plant or plant part thereof of claim 1, wherein said plant part is selected from the group consisting of a cell, pollen, ovule, flower, embryo, leaf, root, stem, shoot, meristem, grain and seed.

4. A method for producing a plant comprising:
a) expressing in a plant cell a recombinant DNA molecule comprising a polynucleotide encoding a polypeptide, wherein the nucleotide sequence encodes a protein with at least 95% identity to SEQ ID NO: 6 or 11; and
b) growing a plant from said plant cell, wherein said plant comprises an enhanced trait selected from increased yield under non-stress conditions, increased yield under water deficit stress, and increased water use efficiency as compared to a control plant, wherein said recombinant DNA molecule provides said increased yield under water deficit stress and said increased water use efficiency, and wherein said plant is selected from the group consisting of corn, soybean, cotton, canola, rice, barley, oat, wheat, turf grass, alfalfa, sugar beet, sunflower, *quinoa* and sugar cane.

5. A method for increasing yield under water deficit stress or increasing water use efficiency in a plant comprising:
crossing a plant comprising a recombinant DNA molecule comprising a polynucleotide encoding a polypeptide with at least 95% identity to SEQ ID NO: 6 or 11, with itself, a second plant from the same plant line, a wild type plant, or a second plant from a different line of plants to produce a seed, wherein said polypeptide comprises a Myb-domain;
growing said seed to produce a plurality of progeny plants; and
selecting a progeny plant with increased yield under water deficit stress or increased water use efficiency relative to a control plant of the same species lacking said recombinant DNA molecule;
wherein said recombinant DNA molecule provides said increased yield under water deficit stress and said increased water use efficiency; and
wherein said plant is selected from the group consisting of corn, soybean, cotton, canola, rice, barley, oat, wheat, turf grass, alfalfa, sugar beet, sunflower, *quinoa* and sugar cane.

6. The method of claim 5, wherein said plant and said second plant are monocot plants.

7. The method of claim 5, wherein said plant and said second plant are maize plants.

8. The method of claim 5, wherein said polynucleotide encodes a polypeptide having an amino acid sequence with at least 97% identity to SEQ ID NO: 6.

9. The method of claim 5, wherein said polynucleotide encodes a polypeptide having an amino acid sequence with at least 98% identity to SEQ ID NO: 6.

10. The method of claim 5, wherein said polynucleotide comprises the nucleotide sequence of SEQ ID NO: 5.

11. The method of claim 5, wherein said polynucleotide encodes a polypeptide comprising the amino acid sequence of SEQ ID NO: 6.

12. The method of claim 5, wherein said method comprises selecting a progeny plant with increased yield under water deficit stress.

13. The method of claim 5, wherein said method comprises selecting a progeny plant with increased water use efficiency.

14. The plant of claim 1, wherein said recombinant DNA molecule comprises SEQ ID NO: 5.

15. The plant of claim 1, wherein said recombinant DNA molecule comprises a polynucleotide that encodes a protein having the amino acid sequence of SEQ ID NO: 6 or 11.

16. The plant of claim 1, wherein said enhanced trait comprises increased yield under water deficit stress.

17. The plant of claim 1, wherein said enhanced trait comprises increased water use efficiency.

18. The plant of claim 1, wherein said enhanced trait comprises increased yield under non-stress conditions.

19. The method of claim 4, wherein said recombinant DNA molecule comprises SEQ ID NO: 5.

20. The method of claim 4, wherein said recombinant DNA molecule comprises a polynucleotide that encodes a protein having the amino acid sequence of SEQ ID NO: 6 or 11.

21. The method of claim 4, wherein said plant is a monocot plant.

* * * * *